US009987227B2

(12) United States Patent
Cipolla et al.

(10) Patent No.: US 9,987,227 B2
(45) Date of Patent: Jun. 5, 2018

(54) INHALED SURFACTANT-MODIFIED LIPOSOMAL FORMULATIONS PROVIDING BOTH AN IMMEDIATE AND SUSTAINED RELEASE PROFILE

(71) Applicant: ARADIGM CORPORATION, Hayward, CA (US)

(72) Inventors: David C. Cipolla, San Ramon, CA (US); Igor Gonda, San Francisco, CA (US)

(73) Assignee: ARADIGM CORPORATION, Hayward, CA (US)

( * ) Notice: Subject to any disclaimer, the term of this patent is extended or adjusted under 35 U.S.C. 154(b) by 790 days.

(21) Appl. No.: 14/506,181

(22) Filed: Oct. 3, 2014

(65) Prior Publication Data

US 2015/0110855 A1   Apr. 23, 2015

Related U.S. Application Data

(60) Provisional application No. 61/894,165, filed on Oct. 22, 2013, provisional application No. 61/949,032, filed on Mar. 6, 2014.

(51) Int. Cl.

| *A61K 9/127* | (2006.01) |
|---|---|
| *A61K 31/496* | (2006.01) |
| *A61K 47/10* | (2017.01) |
| *A61K 47/26* | (2006.01) |
| *A61K 9/00* | (2006.01) |

(52) U.S. Cl.
CPC .......... *A61K 9/127* (2013.01); *A61K 9/0078* (2013.01); *A61K 31/496* (2013.01); *A61K 47/10* (2013.01); *A61K 47/26* (2013.01)

(58) Field of Classification Search
CPC ..................................... A61K 9/127
See application file for complete search history.

(56) References Cited

U.S. PATENT DOCUMENTS

| 5,006,343 | A | | 4/1991 | Benson et al. |
| 5,401,511 | A | | 3/1995 | Margalit |
| 5,643,599 | A | * | 7/1997 | Lee ........................ A61K 9/127 424/450 |
| 5,823,178 | A | | 10/1998 | Lloyd et al. |

(Continued)

FOREIGN PATENT DOCUMENTS

| CA | 2101241 | 7/1993 |
| CA | 2215716 | 9/1997 |

(Continued)

OTHER PUBLICATIONS

Bangham et al., "Diffusion of Univalent Ions across the Lamellae of Swollen Phospholipids" J. Mol. Biol., 13:238-252 (1965).

(Continued)

*Primary Examiner* — Gollamudi Kishore
(74) *Attorney, Agent, or Firm* — Karl Bozicevic; Bozicevic Field & Francis LLP

(57) ABSTRACT

Methods for formulating and compositions of immediate and sustained release liposomal products which comprise a surfactant that interacts with liposomes to effect drug release therefrom, and delivery of such for treatment of respiratory tract infections and other medical conditions, and devices and formulations used in connection with such are described.

16 Claims, 12 Drawing Sheets

(56) References Cited

U.S. PATENT DOCUMENTS

| | | | |
|---|---|---|---|
| 6,197,333 | B1 | 3/2001 | Onyuksel et al. |
| 6,221,385 | B1 | 4/2001 | Camu et al. |
| 6,316,024 | B1 | 11/2001 | Allen et al. |
| 6,355,267 | B1 | 3/2002 | Collins |
| 6,534,018 | B1 | 3/2003 | Baker et al. |
| 6,623,671 | B2 | 9/2003 | Coe et al. |
| 6,759,057 | B1 | 7/2004 | Weiner et al. |
| 6,770,291 | B2 | 8/2004 | Smyth-Templeton et al. |
| 6,855,296 | B1 | 2/2005 | Baker et al. |
| 6,890,555 | B1 | 5/2005 | Desai et al. |
| 7,238,366 | B1* | 7/2007 | Zou ............... A61K 9/1272 264/4.1 |
| 8,119,156 | B2 | 2/2012 | Cipolla et al. |
| 8,268,347 | B1 | 9/2012 | Cipolla et al. |
| 8,414,915 | B2 | 4/2013 | Cipolla et al. |
| 2003/0224039 | A1 | 12/2003 | Boni et al. |
| 2004/0009126 | A1 | 1/2004 | Pilkiewicz et al. |
| 2004/0142026 | A1 | 7/2004 | Boni et al. |
| 2005/0025822 | A1* | 2/2005 | Wong ............... A61K 9/0078 424/450 |
| 2005/0214224 | A1* | 9/2005 | Weers ............... A61K 9/0075 424/45 |
| 2006/0073198 | A1 | 4/2006 | Boni et al. |
| 2006/0280691 | A1* | 12/2006 | Wang ............... A61K 9/0075 424/46 |
| 2007/0077290 | A1 | 4/2007 | Li et al. |
| 2007/0196461 | A1 | 8/2007 | Weers |
| 2009/0246279 | A1 | 10/2009 | Kong et al. |
| 2009/0269396 | A1 | 10/2009 | Cipolla et al. |
| 2009/0274754 | A1 | 11/2009 | Cipolla et al. |
| 2010/0310636 | A1* | 12/2010 | Sharma ............... A61K 9/1271 424/450 |
| 2011/0150983 | A1 | 6/2011 | Cipolla et al. |
| 2013/0129812 | A1* | 5/2013 | Ozpolat ............... C07D 209/14 424/450 |
| 2015/0224169 | A1* | 8/2015 | Bhatia ............... A61K 38/12 514/16.5 |

FOREIGN PATENT DOCUMENTS

| | | |
|---|---|---|
| CA | 2174803 | 10/1997 |
| CN | 1747738 | 3/2006 |
| CN | 102327269 * | 1/2012 |
| EP | 0652008 | 5/1995 |
| EP | 1083881 | 3/2001 |
| EP | 1190705 | 3/2002 |
| EP | 1083886 | 4/2003 |
| EP | 0825852 | 7/2004 |
| WO | 99/51202 | 10/1999 |
| WO | 01/00173 | 1/2001 |
| WO | 01/15678 | 3/2001 |
| WO | 2010/111641 | 9/2001 |
| WO | 2004/110346 | 12/2004 |
| WO | 2004/110493 | 12/2004 |
| WO | 2011/050206 | 4/2011 |
| WO | 2012/050945 | 4/2012 |
| WO | 2012/118376 * | 9/2012 |

OTHER PUBLICATIONS

Conley et al., "Aerosol Delivery of Liposome-Encapsulated Ciprofloxacin: Aerosol Characterization and Efficacy against Francisella tularensis Infection in Mice" Antimicrobial Angents, 41(6):1288-1292 (Jun. 1997).

Desai et al., "A Novel Approach to the Pulmonary Delivery of Liposomes in Dry Powder Form to Eliminate the Deleterious Effects of Milling" Journal of Pharmaceutical Sciences, 91(2):482-491 (Feb. 2002).

Desai et al., "A facile method of delivery of liposomes by nebulization" Journal of Controlled Release, 84:69-78 (2002).

Wong et al., "Liposome delivery of ciprofloxacin against intracellular Francisella tularensis infection" Journal of Controlled Release, 92:265-273 (2003).

Lipuma JJ., Microbiological and immunologic considerations with aerosolized drug delivery. Chest. Sep. 2001;120(3 Suppl):118S-123S.

Moss RB., Administration of aerosolized antibiotics in cystic fibrosis patients. Chest. Sep. 2001;120(3 Suppl):107S-113S.

Smith AL, et al. Safety of aerosol tobramycin administration for 3 months to patients with cystic fibrosis. Ped Pulmonol. 1989;7(4):265-271.

Van Heeckeren AM, et al. Role of Cftr genotype in the response to chronic Pseudomonas aeruginosa lung infection in mice. Am J Physiol Lung Cell Mol Physiol. Nov. 2004;287(5):L944-52. Epub Jul. 9, 2004.

Van Heeckeren AM, et al.. Delivery of CTFR by adenoviral vector to cystic fibrosis mouse lung in a model of chronic Pseudomonas aeruginosa lung infection. Am J Physiol Lung Cell Mol Physiol. Apr. 2004;286(4):L717-26. Epub Sep. 26, 2003.

Van Heeckeren A, et al.., Effects of bronchopulmonary inflammation induced by pseudomonas aeruginosa on adenovirus-mediated gene transfer to airway epithelial cells in mice. Gene Ther. Mar. 1998;5(3):345-51.

Van Heeckeren AM, et al., Murine models of chronic Pseudomonas aeruginosa lung infection. Lab Anim. Jul. 2002;36(3):291-312.

Van Heeckeren AM, et al., Effect of Pseudomonas infection on weight loss, lung mechanics, and cytokines in mice. Am J Respir Crit Care Med. Jan. 2000;161(1):271.

Weber A, et al., Nebulizer delivery of tobramycin to the lower respiratory tract. Pediatr Pulmonol. May 1994;17(5):331-9.

Elhissi et al., "Formulations generated from ethanol-based proliposomes for delivery via medical nebulizers" Journal of Pharmacy and Pharmacology, Jul. 2006, 58:887-894.

Kyriacos et al., "In Vitro Testing of Ciprofloxacin Formulations and Preliminary Study on BCS Biowaiver" Journal of Food and Drug Analysis, (2009) 17(2): 78-84.

Majumdar et al., "Efficacies of liposome-encapsulated streptomycin and ciprofloxacin against *Mycobacterium avium*-M. intracellulare complex infections in human peripheral blood monocyte/macrophages" Antimicrob. Agents Chemother., (1992) 36(12):2808-2815.

Maurer et al., "Anomalous solubility behavior of the antibiotic ciprofloxacin encapsulated in liposomes: a 1H-NMR study" Biopchimica et Biophysica Acta., (1998) 1374:9-20.

Yim, D. et al., "The development of inhaled liposome-encapsulated ciprofloxacin to treat cystic fibrosis." Respiratory Drug Delivery (2006) 2006:425-428.

Serisier, DJ, et al. "Inhaled, Dual-Release Liposomal Ciprofloxacin in Non-Cystic Fibrosis Bronchiectasis (ORBIT-2)—a Randomised, Double-Blind, Placebo-Controlled Trial. Thorax." (2013) 68(9):812-817 doi: 10.1136/thoraxjnl-2013-203207.

Hamblin, AJ, et al., "Efficacy of Inhaled Liposome-Encapsulated Ciprofloxacin Against Yersinis pestis." 19th Congress of the International Society of Aerosols in Medicine (2012) 1 page.

Bruineberg, P, et al. "Inhaled liposomal ciprofloxacin: once a day management of respiratory infections." Respiratory Drug Delivery (2010) pp. 73-81. Editors, Richard N. Dalby, Peter R. Byron, Joanne Peart, Julie D. Suman, Stephen J. Farr, Paul M. Young. Davis Healthcare Int'l Publishing, River Grove, IL. Orlando, FL, Apr. 25-29, 2010.

Cipolla, D, et al. "Liposomes, niosomes and proniosomes—a critical update of their (commercial) development as inhaled products." Respiratory Drug Delivery Europe (2011) pp. 41-54. Editors, Richard N. Dalby, Peter R. Byron, Joanne Peart, Julie D. Suman, Stephen J. Farr, Paul M. Young. Davis Healthcare Int'l Publishing, River Grove, IL. Berlin, Germany, May 3-6, 2011.

Cipolla, D. et al. "Liposomal Ciprofloxacin for Inhalation Retains Integrity Following Nebulization." Respiratory Drug Delivery Europe (2013) pp. 237-242. Editors, Richard N. Dalby, Peter R. Byron, Joanne Peart, Julie D. Suman, Stephen J. Farr, Paul M. Young. Davis Healthcare Int'l Publishing, River Grove, IL. Berlin, Germany, May 21-24, 2013.

Cipolla, D, et al., "Liposomal Formulations for Inhalation." Therapeutic Delivery (2013) 4(8):1047-1072. doi: 10.4155/tde.13.71.

Cipolla, D. et al. "Inhaled Antibiotics to Treat Lung Infection" Pharmaceutical Patent Analyst. (2013) 2(5):647-663.

(56) References Cited

OTHER PUBLICATIONS

Velluto, D., C. et al. "Use of simple kinetic and reaction-order measurements for the evaluation of the mechanism of surfactant-liposome interactions." J Phys Chem B (2011) 115(25): 8130-8137.
Memoli et al., "Surfactant-induced leakage from liposomes: A comparison among different lecithin vesicles" Int. J. Pharm. (1999) 184(2):227-235.
Ruiz et al., "Surfactant-induced release of liposomal contents: A survey of methods and results," Biochim. Biophys. Acta. (1988) 937(1):127-134. (Abstract Only).

\* cited by examiner scale bar = 100 nm scale bar = 200 nm scale bar = 200 nm scale bar = 100 nm

INHALED SURFACTANT-MODIFIED LIPOSOMAL FORMULATIONS PROVIDING BOTH AN IMMEDIATE AND SUSTAINED RELEASE PROFILE

FIELD OF THE INVENTION

Pharmaceutical compositions, and their methods of preparation, comprising the addition of surfactants to liposomal formulations are disclosed. Immediate and sustained release anti-infectives are combined and delivered by inhalation for the treatment of cystic fibrosis (CF), non-CF bronchiectasis, severe COPD, and nontuberculous mycobacterial (NTM) disease.

BACKGROUND OF THE INVENTION

Respiratory tract infections are caused by a variety of microorganisms. Such infections have a myriad of consequences for the community including increased treatment burden and cost, and for the patient in terms of more invasive treatment paradigms and potential for serious illness or even death. It is unfortunate that deliberate infections by lethal inhaled microorganisms have been used in attacks against humans and continue to be a serious security threat. An effective broad-spectrum prophylaxis and treatment against such threats would be very valuable.

As an example of a serious health care burden, high rates of pulmonary colonization with *Pseudomonas aeruginosa* and the difficulty in eradicating those infections, can lead to declines in lung function, increased number and/or frequency of exacerbations, increased hospitalization and a general decline in health in patients with cystic fibrosis (CF), non-CF bronchiectasis, and patients suffering from severe Chronic Obstructive Pulmonary Disease (COPD). Other lung infections including non-tuberculous mycobacteria (NTM) infections also have the potential to increase morbidity and mortality. These issues have necessitated a search for safe and effective inhaled antibiotics to more effectively treat their lung infections.

There are two currently approved inhaled antibiotics for treating CF infection: the aminoglycoside tobramycin (TOBI), and the monobacatam aztreonam lysine (Cayston). Cayston is approved for thrice-daily inhaled treatment while TOBI is given twice-daily. It would be ideal if there were additional inhaled antibiotic options for CF patients which were more convenient (e.g., once-daily), or more effective, than the currently approved inhaled antibiotics. Additionally, there are no inhaled antibiotics approved for non-CF bronchiectasis patients.

Ciprofloxacin is a fluoroquinolone antibiotic that is indicated for the treatment of lower respiratory tract infections due to *P. aeruginosa*, which is common in patients with CF and non-CF bronchiectasis. Ciprofloxacin is broad spectrum and, in addition to *P. aeruginosa*, is active against several other types of gram-negative and gram-positive bacteria. Thus, CF patients who have developed resistance to the aminoglycoside tobramycin (TOBI), or aztreonam lysine (Cayston), can likely still be treated with ciprofloxacin. There is no known cross-resistance between ciprofloxacin and other classes of antimicrobials.

Despite its attractive antimicrobial properties, oral and/or IV ciprofloxacin can produce bothersome side effects, such as GI intolerance (vomiting, diarrhea, abdominal discomfort), as well as dizziness, insomnia, irritability and increased levels of anxiety. There is a clear need for improved treatment regimes that can be used chronically, without resulting in these debilitating side effects. Delivering ciprofloxacin as an inhaled aerosol has the potential to address these concerns by compartmentalizing the delivery and action of the drug in the respiratory tract, which is the primary site of infection.

Currently there is no aerosolized form of ciprofloxacin with regulatory approval for human use, capable of targeting antibiotic delivery direct to the area of primary infection. In part this is because bitterness of the drug has inhibited development of a formulation suitable for inhalation. Furthermore, the drug residence time in the lung is too short to provide additional therapeutic benefit over drug administered by oral or IV routes. Thus, there have been efforts to develop liposomal formulations of ciprofloxacin with improved therapeutic and convenience properties (Yim et al, 2006; Serisier et al, 2013; Bruinenberg et al., 2011; Cipolla et al., 2011, 2013a, 2013b; Cipolla and Chan, 2013).

There are a variety of formulation technologies that have been evaluated for their ability to modulate the release properties of pharmaceutical drugs, or target delivery to specific organs or cells, including liposomes (Drummond et al. 2000). Phospholipid vehicles as drug delivery systems were rediscovered as "liposomes" in 1965 (Bangham et al., 1965). The therapeutic properties of many active pharmaceutical ingredients (APIs) can be improved by their incorporation into liposomal drug delivery systems. The general term liposome covers a wide variety of structures, but generally all are composed of one or more lipid bilayers enclosing an aqueous space in which drugs can be encapsulated.

Liposome encapsulation improves biopharmaceutical characteristics through a number of mechanisms including altered drug PK and biodistribution, sustained drug release from the carrier, enhanced delivery to disease sites, and protection of the active drug species from degradation. A wide variety of drugs have been formulated into liposomes including small molecules, peptides, and nucleic acids; hydrophilic drugs are generally dissolved in the aqueous compartment while hydrophobic drugs are associated with the lipid bilayers (Drummond et al. 2000, Cipolla et al. 2013b). Liposome formulations of the anticancer agents doxorubicin (Myocet®/Evacet®, Doxyl®/Caelyx®), daunorubicin (DaunoXome®), and vincristine sulfate (Marquibo®), the anti-fungal agent amphotericin B (Abelcet®, AmBisome®, Amphotec®) and a benzoporphyrin (Visudyne®) are examples of successful products introduced into the US, European and Japanese markets over the last two decades. The proven safety and efficacy of lipid-based carriers make them attractive candidates for the formulation of pharmaceuticals.

The physicochemical properties of liposomes, and in particular their drug release profile, can be engineered into the formulation via a variety of strategies including: the liposomal composition (e.g., an increase in the acyl chain length of phosphatidylcholine (PC) reduced the release rate of liposomal vincristine (Boman et al. 1993)), the presence and concentration of sterol (e.g., the addition of 30% cholesterol reduces membrane permeability leading to a slower drug release rate for many liposomal formulations), surface modification with polyethyleneglycol (PEG) (e.g., doxorubicin liposomes containing PEG had longer circulation half-lives and slower release than egg PC/cholesterol liposomes (Abraham et al. 2005)), liposomal size and lamellarity (e.g., unilamellar liposomes typically release their contents at a faster rate than multilamellar vesicles), the drug to lipid ratio (e.g., higher drug to lipid ratios reduced the release rate of liposomal vincristine, and were also found to increase its efficacy (Johnston et al. 2006)), the state of the drug inside the vesicle (e.g., liposomes containing precipitated doxorubicin had slower release than those with doxorubicin in solution (Lasic et al. 1995)), the choice of drug loading method (e.g., a larger transmembrane pH gradient reduced the release rate of liposomal doxorubicin (Mayer et al. 1990)), and other factors including osmolarity, pH, and choice of buffer and excipients. We were interested to see if the encapsulation state and release properties of a liposomal ciprofloxacin formulation could be modified by addition of surfactants.

A number of US patents describe liposomal formulations for inhalation: U.S. Pat. Nos. 8,414,915; 8,268,347; 8,119,156; and 8,071,127. These patents describe formulations of liposomal ciprofloxacin and mixtures of liposomal ciprofloxacin with free ciprofloxacin. These liposome formulations were designed to be robust to the nebulization process such that the encapsulation of drug was principally unaltered. In comparison to the current oral or IV ciprofloxacin formulations, a liposomal ciprofloxacin aerosol formulation should offer several benefits: 1) higher drug concentrations in the lung, 2) increased drug residence time via sustained release at the site of infection, 3) decreased side effects, 4) increased palatability, 5) better penetration into the bacteria, and 6) better penetration into the cells infected by bacteria. It has previously been shown that inhalation of liposome encapsulated fluoroquinolone antibiotics may be effective in treatment of lung infections and in a mouse model of *F. tularensis* liposomal encapsulated fluoroquinolone antibiotics were shown to be superior to the free or unencapsulated fluoroquinolone by increasing survival (CA2,215,716, CA2,174,803, and CA2,101,241).

Another group of US patents describe inhaled formulations of liposomal aminoglycosides for treatment of lung infections: U.S. Pat. Nos. 8,226,975, 7,879,351, and 7,718,189.

However, there remain opportunities to develop novel liposomal formulations with improved properties and release characteristics, one of those being the ability to modify their properties in a simple and flexible manner. We describe a strategy that we have used to develop these new liposomal formulations through the addition of surfactant. The addition of surfactant to the pre-existing liposomal formulation, when properly designed and executed, can allow for the amount of free drug and the release profile to be tailored into the product.

There is an extensive history of detergents being used to solubilize biological membranes to allow for elucidation of membrane structure and function (Helenius and Simons 1975). The ability of surfactants to solubilize phospholipids, specifically, was reviewed (Lichtenberg et al. 1983). Typically, as surfactant is added to phospholipids, surfactant initially partitions between the solution and the phospholipid bilayers and the bilayer permeability may increase without loss of structure (Lichtenberg et al. 1983). Once the phospholipid bilayers become saturated with surfactant, addition of more surfactant leads to the formation of mixed micelles of surfactant and phospholipid until all of the remaining surfactant-saturated bilayers are converted to mixed micelles. Any further addition of surfactant leads to a decrease in the size of the micelles as they become more dilute in phospholipid content. Vesicle-surfactant systems have frequently been characterized by monitoring their light scattering properties, with maximum turbidity generally associated with the surfactant saturated bilayer state (Velluto, Gasbarri et al. 2011) followed by a rapid decline in turbidity once the bilayers are completely solubilized by surfactant (Paternostre et al. 1988, Ribosa et al. 1992, Lasch 1995, Cho et al. 1999, Deo and Somasundaran 2003).

Liposomes have been used as a simplified model of biological membranes. Interest in the development of antimicrobials that would function by disruption of the bacterial membrane spurred a better understanding of the interaction of surfactant-like molecules with liposomes (Nagawa and Regen 1992, Liu and Regen 1993). In addition, liposomes were being investigated as drug delivery vehicles so knowledge of the factors which affected the timing and rate of release of the encapsulated drug is paramount. After in vivo administration, liposomes come into contact with many natural amphiphiles present in physiological fluids. Surfactants can be used as a simplification to the complex biological milieu, allowing for characterization of drug release from liposomes in the presence of surfactant (Ruiz et al. 1988).

Two release mechanisms were identified for liposome-encapsulated carboxyfluorescein (CF) in response to added surfactant (Nagawa and Regen 1992). For some combinations of liposomes and surfactant, there was a gradual release of the encapsulated agent from all vesicles with increasing surfactant concentration. For other combinations, there was a catastrophic rupture in which a subset of the vesicles rapidly released their entire encapsulated payload while others were unaffected. These findings were expanded by showing that Triton X-100 in its monomeric form (below its CMC) induced leakage of CF from all liposomes that were studied, but when Triton X-100 was in its micellar form (above its CMC) it was able to rupture only gel-phase vesicles (below the Tm) and compact fluid-phase vesicles (i.e., those containing significant cholesterol) but not fluid-phase liposomes (Liu and Regen 1993). The properties of the encapsulated agent can also influence its release behavior. More surfactant was required to release an equivalent percentage of a larger molecule, dextran, versus a smaller molecule, glucose (Ruiz, et al. 1988). Finally, the kinetics of release of CF using sublytic concentrations of Triton X-100 was explored for both sonicated and extruded liposomes composed of egg or soy PC (Memoli et al. 1999). In both cases, release of CF was almost instantaneous and reached a stable value within a few minutes, suggesting that transient holes were formed upon association of low levels of surfactant with liposomes but these holes then closed limiting further release of CF (Memoli et al. 1999). In contrast, upon addition of solubilizing levels of surfactant, there was a complete breakdown of liposome structure within 0.2 sec with complete release of encapsulated drug (Velluto et al. 2011). While interactions of surfactants with liposomes have been more fully explored from a mechanistic basis, there has been little interest in utilizing this property of surfactants to modify the encapsulation state and release properties of liposomes for therapeutic purposes.

We describe the development of new liposomal formulations of ciprofloxacin containing surfactants to modify their release properties. Liposomal ciprofloxacin is in development as a once-daily inhaled antibiotic to treat respiratory infections in indications such as cystic fibrosis (CF) and non-CF bronchiectasis (Bruinenberg et al., 2011, Cipolla et al., 2011, Cipolla and Chan, 2013, Cipolla et al., 2013b, Serisier et al., 2013, Yim et al., 2006); it also appears to be effective against a variety of potential bioterrorism infections including tularemia (Conley et al. 1997) and plague (Hamblin et al., 2013). In contrast, currently approved inhaled antibiotics for cystic fibrosis are not encapsulated in liposomes and must be administered twice- or thrice-daily (Cipolla and Chan, 2013). These antibiotics failed to show adequate efficacy and safety for approval outside cystic fibrosis (Cipolla and Chan, 2013). There are two liposomal ciprofloxacin formulations being investigated in the clinic: Lipoquin™, for which all of the ciprofloxacin is encapsulated into liposomes and a combination formulation, termed Pulmaquin™ which contains both a mixture of free, unencapsulated ciprofloxacin and liposome-encapsulated ciprofloxacin. We were motivated to determine if we could apply the inventive step to modify the Lipoquin formulation specifically through the addition of surfactant to create a mixture of both free and encapsulated ciprofloxacin in varying portions, and which may possess modified release properties compared to Lipoquin or Pulmaquin. Additionally, we investigated whether such formulations could be designed to retain their physical properties after long term refrigerated storage as well as after nebulization to create an inhalation aerosol. We also believe that the learnings from the addition of surfactant to liposomal ciprofloxacin formulations can be broadly applied to liposomal systems in general and to treat a wide variety of indications, not limited to lung infections or administration through the inhalation route.

SUMMARY OF THE INVENTION

A composition is disclosed which composition may be a formulation designed for aerosolized delivery to a human patient. The formulation may be a composition comprised of liposomes which encapsulate a drug. The same drug may be present as free drug within the formulation with the free drug and liposomes held within a pharmaceutically acceptable excipient carrier. The drug has a pharmacological effect whereas the carrier is not active. The formulation includes a surfactant which interacts with the liposomes in a manner which affects the release of drug from the liposomes and thereby affects the drug release profile of the formulation when administered to the lungs of a patient.

Different compounds can be used for the construction of the liposomes and different surfactants can be used. A useful surfactant is polysorbate 20 present in a relatively small amount such as in a range of 0.01% to 5% by weight or 0.05% to 1% by weight. The inclusion of a surfactant such as tween 20 can be either a percentage weight (weight/weight) or volume percentage (v/v). However, because the density of the surfactant is approximately 1 g/ml different nomenclatures can be used.

Different drugs can be included within the formulation. An example of a useful drug is ciprofloxacin which is present in a free form as free ciprofloxacin (FCI) as well as in an encapsulated form referred to as liposomal ciprofloxacin (CFI). The free ciprofloxacin may be present in an amount sufficient to provide an initial therapeutic dose to the patient with the remainder of the ciprofloxacin being encapsulated within the liposomes. The encapsulated drug is released slowly over time to maintain a therapeutic level of the drug in the patient without either dropping below preferred therapeutic levels or rising above levels which result in adverse effects. For a formulation for pulmonary delivery the encapsulated ciprofloxacin (CFI) may be present in a concentration of 10 to 20 mg/ml combined with 0.1 to 1.0% by weight of polysorbate 20 in a formulation having a pH in a range of 4.5 to 5.5.

There is some significance to the ratio of the amount of surfactant to the amount of liposomes and the ratio may be in the range of surfactant to liposomes of 1:1000 to 1:1, or 1:100 to 1:2, or 1:20 to 1:4 based on the mass of the surfactant and liposomes.

The free ciprofloxacin may be present in an amount in a range of from 5% to 50% and the encapsulated ciprofloxacin may be present in an amount of 50% to 95% based on the total amount of ciprofloxacin or drug in the formulation. The ratio may be in the range of about 30% free drug±20% to 70% encapsulated drug±20% such as 30% free ciprofloxacin±20% to 70% encapsulated ciprofloxacin±20%.

Examples of specific liposome compositions are provided within the examples. The liposome is constructed such that when the formulation is aerosolized the liposomes maintain their structural integrity with results showing that 90% or more of the liposomes maintain structural integrity when aerosolized, or 95% or more of the liposomes, or 98% or more of the liposomes maintain their structural integrity after aerosolization.

A useful formulation of the invention can include a pharmaceutically acceptable excipient useful for aerosolized delivery to the lungs which has therein free ciprofloxacin in an amount of 30% and liposome encapsulated ciprofloxacin in an amount of 70% based on the total weight of all ciprofloxacin within the formulation with the formulation being further comprised of polysorbate 20 and having a pH in the range of 4.5 to 5.5.

Formulations comprised of surfactants and liposomes which are delivered via an aerosol to the lungs of a human patient or by various alternative administration routes are delivered. The liposomal formulations containing encapsulated drug are modified by the addition of surfactants to cause transient release of a given percentage of the encapsulated drug, which contributes to an immediate release component, while the remaining liposome encapsulated drug provides a sustained release component. By varying the composition of the surfactant, its concentration, the osmolarity or tonicity of the liposomal formulation, as well as the pH, the amount of encapsulated and free drug can is designed into the formulation. Additionally, the association of surfactant with the liposomes modulates the release profile of the remaining encapsulated drug. The choice of drug is not limited to anti-infectives, and is not specific to any class of therapeutic agent.

We also describe novel methods of preparation of surfactant associated liposomal formulations. Typically the cholesterol, lipids, and other components used in the composition of the liposomes are all added during the liposomal manufacturing process. However, we describe here another aspect of the invention which is to add the surfactant post manufacture of the liposomal product. Thus, the choice of surfactant, and its concentration can be selected at a later date to add to the liposomes to alter the state of drug encapsulation or modulate the release profile of the active agent. The surfactants can be added immediately after liposome manufacture, or many years later, just prior to use, or months or years in advance of the liposomal product being used to treat a subject or patient. The advantage of our invention is that the manufacture of liposomes is often complicated. It is therefore much preferred to add the surfactant as a modifier to an already developed liposomal formulation to modulate its properties, instead of developing the new liposomes containing the surfactant via a new manufacturing process that could be risky and costly.

Another aspect of the invention is that the addition of the surfactant is at a concentration that does not lyse the liposome, but results in liposomes retaining their vesicle size, shape, and lamellarity, but with altered drug encapsulation and/or drug release rate profiles.

The liposomes may be unilamellar or multilamellar, and may be bioadhesive, containing a molecule such as hyaluronic acid. At least one therapeutic agent in addition to the free and liposome-encapsulated anti-infective may also be included in the composition. That therapeutic agent may be free drug or encapsulated drug present with a pharmaceutically acceptable carrier useful for direct inhalation into human lungs. The other drugs may include enzymes to reduce the viscoelasticity of the mucus such as DNase or other mucolytic agents, chemicals to upregulate the chloride ion channel or increase flow of ions across the cells, P2Y2 agonists, elastase inhibitors including Alpha-1 antitrypsin (AAT), bronchodilators, steroids, N-acetylcysteine, interferon gamma, interferon alpha, agents that enhance the activity of the antibiotic against biofilm bacteria such as sodium salicylate (Polonio R E et al., 2001), or antibiotics known to those skilled in the art.

A further aspect of the invention is a method for treating lung infections associated with diseases such as cystic fibrosis, non-CF bronchiectasis, or NTM in a patient, the method comprising administering a formulation of surfactant-modified liposomes comprising the anti-infective; e.g., ciprofloxacin, to the patient. The formulation is preferably administered by inhalation to the patient.

According to another aspect of the present invention, a formulation comprising both a free and encapsulated anti-infective provides an initially high therapeutic level of the anti-infective in the lungs to overcome the barrier to eradicate or reduce the levels of undesirable bacteria. The intent of the immediate-release anti-infective, e.g., ciprofloxacin, is thus to rapidly increase the antibiotic concentration in the lung to therapeutic levels. The sustained-release anti-infective; e.g., ciprofloxacin, serves to maintain a therapeutic level of antibiotic in the lung thereby providing continued therapy over a longer time frame, increasing efficacy, reducing the frequency of administration, and reducing the potential for resistant colonies to form. The sustained release of the anti-infective may ensure that the anti-infective agent never falls below the sub-inhibitory concentration and so reduces the likelihood of forming resistance to the anti-infective.

An aspect of the invention is a composition, comprising:
liposomes containing encapsulated drug;
free drug;
a pharmaceutically acceptable excipient; and
a surfactant which interacts with the liposomes to reduce drug encapsulation and modulate drug release from the liposomes.

In another aspect of the invention the composition is aerosolized into particles of formulation.

In another aspect of the invention the liposomes are unilamellar.

In another aspect of the invention the surfactant is selected from the group consisting of alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, polyacrylates, acrylic acid graft copolymers, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes, lignin-sulfite waste liquor, alkyl phosphates, quaternary ammonium compounds, amine oxides, and betaines;
wherein the composition is an inhalation aerosol in particle form.

In another aspect of the invention the ratio of surfactant to liposomes is between about 1:1000 to 1:1.

In another aspect of the invention the ratio of surfactant to liposomes is between about 1:100 and 1:2.

In another aspect of the invention the ratio of surfactant to liposomes is between about 1:20 and 1:4.

In another aspect of the invention the concentration of surfactant is between 0.01 and 2% by volume based on the total formulation volume.

In another aspect of the invention the concentration of surfactant is between about 0.1 and 1% by volume based on the total formulation volume.

In another aspect of the invention the particles of the aerosol have an aerodynamic diameter in a range from about 0.5 microns to about 12 microns.

In another aspect of the invention the particles of the aerosol have an aerodynamic diameter in a range from about 1 micron to about 6 microns.

In another aspect of the invention the particles of the aerosol have an aerodynamic diameter in a range from about 2 microns to about 4 microns.

In another aspect of the invention the encapsulated drug is an anti-infective.

In another aspect of the invention the anti-infective is ciprofloxacin.

In another aspect of the invention the anti-infective is selected from the group consisting of a quinolone, a sulfonamide, an aminoglycoside, a tetracycline, para-aminobenzoic acid, a diaminopyrimidine, a beta-lactam, a beta-lactam and a beta-lactamase inhibitor, chloramphenicol, a macrolide, lincomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, and terbinafine.

In another aspect of the invention the liposomes have a diameter in a range from about 10 nm to about 10 μm.

In another aspect of the invention the liposomes have a diameter in a range from about 20 nm to about 1 μm.

In another aspect of the invention the liposomes are about 100 nm in diameter±20%.

In another aspect of the invention the liposomes further comprise a lipid selected from the group consisting of fatty acids; lysolipids; sphingolipids; phosphatidylcholines; phosphatidylethanolamines; sphingomyelin; glycolipids; glucolipids; glycosphingolipids; phosphatidic acid; palmitic acid; stearic acid; arachidonic acid; oleic acid; lipids bearing sulfonated mono-, di-, oligo- or polysaccharides; lipids with ether and ester-linked fatty acids, polymerized lipids, diacetyl phosphate, stearylamine, cardiolipin, phospholipids with short chain fatty acids of 6 to 8 carbons in length, synthetic phospholipids with asymmetric acyl chains; and lipids bearing a covalently bound polymer.

In another aspect of the invention the liposome-encapsulated anti-infective agent is prepared using a phospholipid.

In another aspect of the invention the phospholipid is selected from the groups consisting of phosphatidylcholines, lysophosphatidylcholines, phosphatidylethanolamines, phosphatidylinositols, phosphatidylglycerols, phosphatidic acid, phosphatidylserines, and mixtures thereof.

In another aspect of the invention the phospholipid is provided in admixtures with a modifying agent selected from the group consisting of cholesterols, stearyl amines, stearic acid, tocopherols, and mixtures thereof.

In another aspect of the invention the free drug comprises between about 1 and about 75% of a total of free drug and liposome encapsulated drug.

In another aspect of the invention the free drug comprises between about 5 and about 50% of a total of free drug and liposome encapsulated drug.

In another aspect of the invention the formulation provides in vivo release of 90% of the encapsulated drug a period of between about 1 hour and about 1 week.

In another aspect of the invention the formulation provides in vivo release of 90% of the encapsulated drug a period of between about 8 and 24 hours.

In another aspect of the invention the formulation provide a rate of release of encapsulated drug between 0.1 to 100% per hour.

In another aspect of the invention the formulation provide a rate of release of encapsulated drug between 0.5 and 20% per hour.

In another aspect of the invention the formulation provide a rate of release of encapsulated drug between 2 and 10% per hour, with the near complete release of antibiotic occurring after about 1 to 24 hours.

In another aspect of the invention the surfactant is added to a formulation comprised of liposomes and the surfactant interacts with the liposomes thereby increasing the percentage of unencapsulated free drug in the formulation by about 1 to 50%, or 2 to 25% or 5 to 20%.

In another aspect of the invention the surfactant causes an increase in drug release rate of about 1% to 200% as measured by an IVR assay.

In another aspect of the invention the surfactant causes an increase in drug release rate of about 5% to 50% as measured by an IVR assay.

Another aspect of the invention provides a method of treating or ameliorating a P. aeruginosa infection using the composition as described above.

Another aspect of the method is provided wherein the encapsulated drug is an anti-infective.

Another aspect of the method is provided wherein the anti-infective is ciprofloxacin.

Another aspect of the method is provided wherein the composition is formulated for aerosolized delivery.

Another aspect of the method is provided wherein the liposomes are unilamellar.

Another aspect of the method is provided wherein the surfactant is selected from the group consisting of alkylphenyl alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, polyacrylates, acrylic acid graft copolymers, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes, lignin-sulfite waste liquor, alkyl phosphates, quaternary ammonium compounds, amine oxides, and betaines. The composition of claim 1, wherein the composition is an inhalation aerosol in particle form.

Another aspect of the method is provided wherein the ratio of surfactant to liposomes is between about 1:1000 to 1:1.

Another aspect of the method is provided wherein the ratio of surfactant to liposomes is between about 1:100 and 1:2.

Another aspect of the method is provided wherein the ratio of surfactant to liposomes is between about 1:20 and 1:4.

Another aspect of the method is provided wherein the concentration of surfactant is between 0.01 and 2%.

Another aspect of the method is provided wherein the concentration of surfactant is between about 0.1 and 1%.

Another aspect of the method is provided wherein the particles of the aerosol have a diameter in a range from about 0.5 microns to about 12 microns.

Another aspect of the method is provided wherein the particles of the aerosol have a diameter in a range from about 1 micron to about 6 microns.

Another aspect of the method is provided wherein the particles of the aerosol have a diameter in a range from about 2 microns to about 4 microns.

Another aspect of the method is provided wherein the anti-infective is one or more selected from the group consisting of a quinolone, a sulfonamide, an aminoglycoside, a tetracycline, para-aminobenzoic acid, a diaminopyrimidine, a beta-lactam, a beta-lactam and a beta-lactamase inhibitor, chloramphenicol, a macrolide, lincomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, terbinafine.

Another aspect of the method is provided wherein the liposomes have a diameter in a range from about 10 nm to about 10 μm.

Another aspect of the method is provided wherein the liposomes have a diameter in a range from about 20 nm to about 1 μm.

Another aspect of the method is provided wherein the liposomes are about 100 nm in diameter±20%.

Another aspect of the method is provided wherein said liposomes further comprise a lipid selected from the group consisting of fatty acids; lysolipids; sphingolipids; phosphatidylcholines; phosphatidylethanolamines; sphingomyelin; glycolipids; glucolipids; glycosphingolipids; phosphatidic acid; palmitic acid; stearic acid; arachidonic acid; oleic acid; lipids bearing sulfonated mono-, di-, oligo- or polysaccharides; lipids with ether and ester-linked fatty acids, polymerized lipids, diacetyl phosphate, stearylamine, cardiolipin, phospholipids with short chain fatty acids of 6 to 8 carbons in length, synthetic phospholipids with asymmetric acyl chains; and lipids bearing a covalently bound polymer.

Another aspect of the method is provided wherein the liposome-encapsulated anti-infective agent is prepared using a phospholipid.

Another aspect of the method is provided wherein said phospholipid is selected from the groups consisting of phosphatidylcholines, lysophosphatidylcholines, phosphatidylethanolamines, phosphatidylinositols, phosphatidylglycerols, phosphatidic acid, phosphatidylserines, and mixtures thereof.

Another aspect of the method is provided wherein said phospholipid is provided in admixtures with a modifying agent selected from the group consisting of cholesterols, stearyl amines, stearic acid, tocopherols, and mixtures thereof.

Another aspect of the method is provided wherein the free drug comprises between about 1 and about 75% of a total of free drug and liposome encapsulated drug.

Another aspect of the method is provided wherein the free drug comprises between about 5 and about 50% of a total of free drug and liposome encapsulated drug.

Another aspect of the method is provided wherein the in vivo release of 90% of the encapsulated drug is between about 1 hour and about 1 week.

Another aspect of the method is provided wherein the in vivo release of 90% of the encapsulated drug is between about 8 and 24 hours.

Another aspect of the method is provided wherein the rate of release of the encapsulated drug is between 0.1 to 100% per hour Another aspect of the method is provided wherein the rate of release of the encapsulated drug is between 0.5 and 20% per hour.

Another aspect of the method is provided wherein the rate of release of the encapsulated drug is between 2 and 10% per hour, with the near complete release of antibiotic occurring after about 1 to 24 hours.

Another aspect of the method is provided wherein the surfactant causes a change in the encapsulation state of about 1 to 50%.

Another aspect of the method is provided wherein the surfactant causes an increase in release rate of about 1% to 200% as measured by an IVR assay.

Another aspect of the method is provided wherein the surfactant causes an increase in release rate of about 5% to 50% as measured by an IVR assay.

Another aspect of the method is provided wherein the drug is selected from the groups consisting of an enzyme, a DNase, a mucolytic agent, chemicals that up-regulate the chloride ion channel or increase flow of ions across the epithelial surface of cells, a bronchodilator, a steroid, a P2Y2 agonist, an elastase inhibitor such as Alpha-1 antitrypsin (AAT), N-acetylcysteine, agents that enhance the activity of the anti-infective against biofilm bacteria such as sodium salicylate, gamma interferon, alpha interferon, a fluoroquinolone or an antibiotic.

Another aspect of the method is provided wherein the drug is a fluoroquinolone selected from the group consisting of amifloxacin, cinoxacin, ciprofloxacin, danofloxacin, difloxacin, enoxacin, enrofloxacin, fleroxacin, irloxacin, lomefloxacin, miloxacin, norfloxacin, ofloxacin, pefloxacin, rosoxacin, rufloxacin, sarafloxacin, sparfloxacin, temafloxacin and tosufloxacin or an antibiotic selected from the group of tobramycin, colistin, azithromycin, amikacin, cefaclor (Ceclor), aztreonam, amoxicillin, ceftazidime, cephalexin (Keflex), gentamicin, vancomycin, imipenem, doripenem, piperacillin, minocycline, or erythromycin.

Another aspect of the invention provides a method of modulating a drug release rate of a formulation, comprising:

providing a formulation comprised of a pharmaceutically acceptable carrier and liposomes, wherein the liposomes are comprised of a drug and phosphatidylcholine;

adding polysorbate 20 to the formulation in an amount of 0.1 to 1% by volume thereby modulating a drug release profile of the liposomes.

Another aspect of the invention further comprises:

administering the formulation to a patient; and adjusting the amount of polysorbate 20 added based on a characteristic of the patient.

Another aspect of the invention is provided wherein the formulation is administered by inhalation and the patient characteristic is lung function.

Another aspect of the invention is provided wherein the patient characteristic is selected from the group consisting of body mass, lean body mass, height, age, gender, renal clearance assessment, liver function assessment, and determined concentration of the drug in patient blood.

Another aspect of the invention is provided wherein the patient characteristic is selected from the group consisting of side effects observed, type of patient infection being treated, and known minimum inhibitory concentrations for the drug.

These and other objects, advantages, and features of the invention will become apparent to those persons skilled in the art upon reading the details of the formulations and methodology as more fully described below.

DETAILED DESCRIPTION OF THE INVENTION

Figure 1:
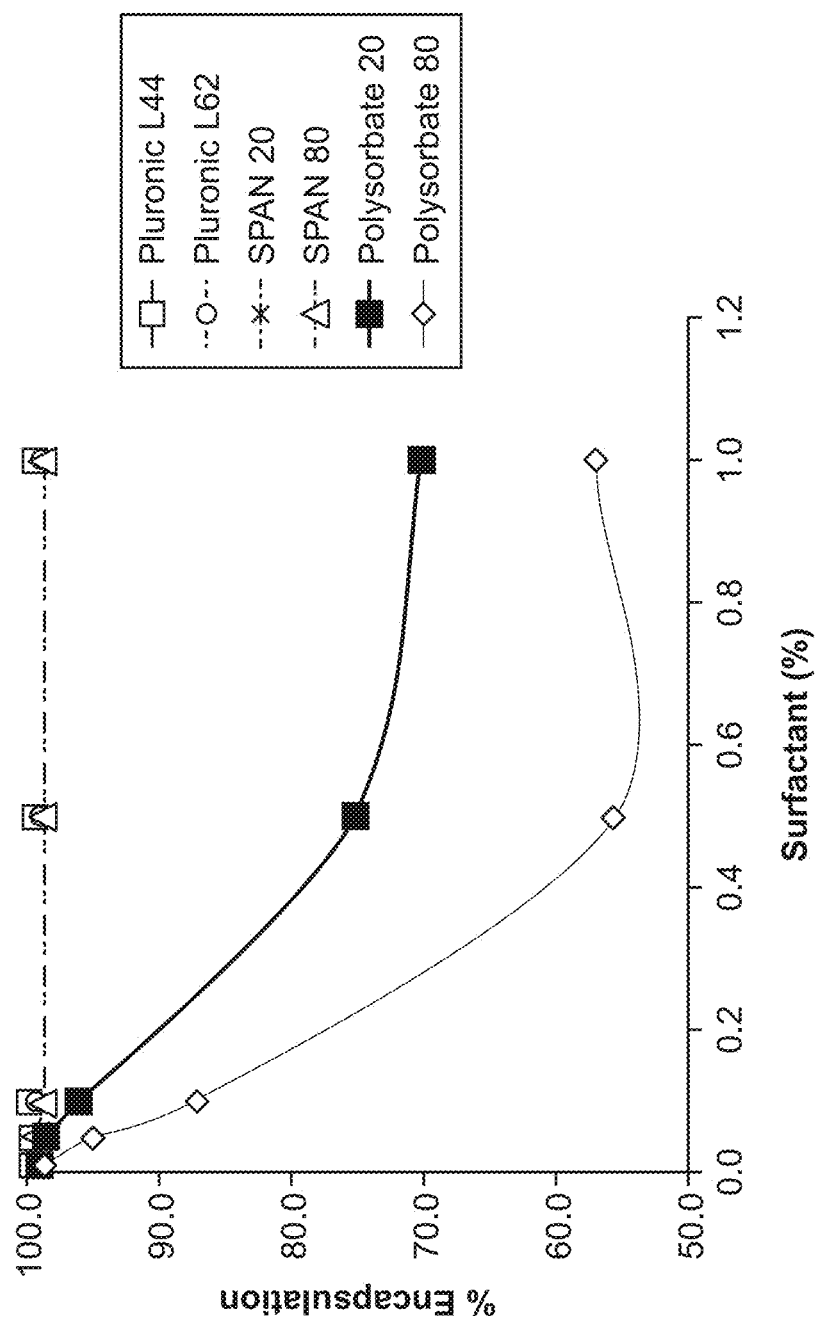
FIG. 1 is a graph showing the effect of addition of various surfactants on the state of ciprofloxacin encapsulation. CFI at 50 mg/ml ciprofloxacin was diluted to a final concentration of ~12.5 mg/ml with water and then either an aliquot of 1% or 10% surfactant to achieve a final surfactant concentration of 0.01, 0.05, 0.1, 0.5 or 1.0%. The surfactants that were investigated included: Pluronic L44, Pluronic L62, SPAN 20, SPAN 80, polysorbate 20 and polysorbate 80. After vortexing and allowing each sample to equilibrate for at least 30 min, the ciprofloxacin encapsulation state was determined by centrifugal filtration in duplicate. There are no data points using 0.5% or 1% SPAN 20 due to poor miscibility of the solution at those concentrations.

Before the present method of formulating surfactant-associated liposomes and delivery of such for prevention and/or treatment of a variety of lung infections associated with diseases such as cystic fibrosis, non-CF bronchiectasis, NTM, and other medical conditions, and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, anti-infective refers to agents that act against infections, such as bacterial, viral, fungal, mycobacterial, or protozoal infections.

Anti-infectives covered by the invention include but are not limited to quinolones (such as nalidixic acid, cinoxacin, ciprofloxacin and norfloxacin and the like), sulfonamides (e.g., sulfanilamide, sulfadiazine, sulfamethaoxazole, sulfisoxazole, sulfacetamide, and the like), aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), para-aminobenzoic acid, diaminopyrimidines (such as trimethoprim, often used in conjunction with sulfamethoxazole, pyrazinamide, and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil, cefinetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chloramphenicol, macrolides (such as erythromycin, azithromycin, clarithromycin, and the like), lincomycin, clindamycin, spectinomycin, polymyxin B, polymixins (such as polymyxin A, B, C, D, E.sub.1(colistin A), or E.sub.2, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Anti-infectives can include antifungal agents, including polyene antifungals (such as amphotericin B, nystatin, natamycin, and the like), flucytosine, imidazoles (such as miconazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed and pharmaceutically acceptable salts thereof and combinations thereof. Discussion and the examples are directed primarily toward ciprofloxacin but the scope of the application is not intended to be limited to this anti-infective. Combinations of drugs can be used.

As used herein, "Formulation" refers to the liposome encapsulated anti-infective, with any excipients or additional active ingredients, either as a dry powder or suspended or dissolved in a liquid.

The term "surfactant" comes from shortening the phrase "surface active agent". In pharmaceutical applications, surfactants are useful in liquid pharmaceutical formulations in which they serve a number of purposes, acting as emulsifiers, solubilizers, and wetting agents. Emulsifiers stabilize the aqueous solutions of lipophilic or partially lipophilic substances. Solubilizers increase the solubility of components of pharmaceutical compositions increasing the concentration which can be achieved. A wetting agent is a chemical additive which reduces the surface tension of a fluid, inducing it to spread readily on a surface to which it is applied, thus causing even "wetting" of the surface with the fluids. Wetting agents provide a means for the liquid formulation to achieve intimate contact with the mucous membrane or other surface areas with which the pharmaceutical formulation comes in contact.

There are many ways that liposomes can be prepared and are well known to the art. Some methods to prepare liposomal ciprofloxacin formulations are described in U.S. Pat. No. 8,414,915. In general, ciprofloxacin is preferably used in the formulations of the instant invention, although other antibiotics or anti-infectives known to those skilled in the art may be used. However, this invention is not limited to liposomal formulations of anti-infectives.

Regardless of the form of the drug formulation, it is preferable to create droplets or particles for inhalation in the range of about 0.5 µm to 12 µm, preferably 1 µm to 6 µm, and more preferably about 2 to 4 µm. By creating inhaled particles which have a relatively narrow range of size, it is possible to further increase the efficiency of the drug delivery system and improve the repeatability of the dosing. Thus, it is preferable that the particles not only have a size in the range of 0.5 µm to 12 µm or 2 µm to 6 µm or about 3 to 4 µm but that the mean particle size be within a narrow range so that 80% or more of the particles being delivered to a patient have a particle diameter which is within ±20% of the average particle size, preferably ±10% and more preferably ±5% of the average particle size.

The formulations of the invention may be administered to a patient using a disposable package and portable, handheld, battery-powered device, such as the AERx device (U.S. Pat. No. 5,823,178). Alternatively, the formulations of the instant invention may be carried out using a mechanical (non-electronic) device. Other inhalation devices may be used to deliver the formulations including conventional jet nebulizers, ultrasonic nebulizers, soft mist inhalers, dry powder inhalers (DPIs), metered dose inhalers (MDIs), condensation aerosol generators, and other systems.

An aerosol may be created by forcing drug through pores of a membrane which pores have a size in the range of about 0.25 to 6 microns (U.S. Pat. No. 5,823,178). When the pores have this size the particles which escape through the pores to create the aerosol will have a diameter in the range of 0.5 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that an object of some embodiments is to provide aerosolized particles having a diameter in the range of about 0.5 to 12 microns.

In an embodiment, a low boiling point, highly volatile propellant is combined with the liposomes of the invention and a pharmaceutically acceptable excipient. The liposomes may be provided as a suspension or dry powder in the propellant, or, in another embodiment, the liposomes are dissolved in solution within the propellant. Both of these formulations may be readily included within a container which has a valve as its only opening. Since the propellant is highly volatile, i.e., has a low boiling point, the contents of the container will be under pressure.

In accordance with another formulation, the ciprofloxacin-containing liposomes are provided as a dry powder by itself, and in accordance with still another formulation, the ciprofloxacin-containing liposomes are provided in a solution formulation. The dry powder may be directly inhaled by allowing inhalation only at the same measured inspiratory flow rate and inspiratory volume for each delivery. The powder may be dissolved in an aqueous solvent to create a solution which is moved through a porous membrane to create an aerosol for inhalation.

Any formulation which makes it possible to produce aerosolized forms of ciprofloxacin-containing liposomes which can be inhaled and delivered to a patient via the intrapulmonary route may be used in connection with the present invention. Specific information regarding formulations which can be used in connection with aerosolized delivery devices are described within Remington's Pharmaceutical Sciences, A. R. Gennaro editor (latest edition) Mack Publishing Company.

Based on the above, it will be understood by those skilled in the art that a plurality of different treatments and means of administration can be used to treat a single patient. Thus, patients already receiving such medications, for example, as intravenous ciprofloxacin or antibiotics, etc., may benefit from inhalation of the formulations of the present invention. Some patients may receive only ciprofloxacin-containing liposome formulations by inhalation. Such patients may have symptoms of cystic fibrosis or non-CF bronchiectasis, be diagnosed as having lung infections, or have symptoms of a medical condition, which symptoms may benefit from administration to the patient of an antibiotic such as ciprofloxacin. The formulations of the invention may also be used diagnostically. In an embodiment, for example, a patient may receive a dose of a formulation of the invention as part of a procedure to diagnose lung infections, wherein one or more of the patient's symptoms improves in response to the formulation.

A patient will typically receive a dose of about 0.01 to 10 mg/kg/day of the inhaled liposomal ciprofloxacin formulation, ±20% or ±10%. This dose will typically be administered by at least one, preferably several "puffs" or inhalations from the aerosol device. The total dose per day is preferably administered at least once per day, but may be divided into two or more doses per day. Some patients may benefit from a period of "loading" the patient with ciprofloxacin with a higher dose or more frequent administration over a period of days or weeks, followed by a reduced or maintenance dose. As cystic fibrosis and non-CF bronchiectasis are typically chronic conditions, patients are expected to receive such therapy over a prolonged period of time.

Thus, as discussed above, the formulations according to some aspects of the invention include free or non-encapsulated ciprofloxacin in combination with the liposome-encapsulated ciprofloxacin with ability to modify the drug release profile. Such formulations may provide an immediate benefit with the free ciprofloxacin resulting in a rapid increase in the antibiotic concentration in the lung fluid surrounding the bacterial colonies or biofilm and reducing their viability, followed by a sustained benefit from the encapsulated ciprofloxacin which continues to kill the bacteria or decrease its ability to reproduce, or reducing the possibility of antibiotic resistant colonies arising.

A number of patents have described specific formulations of liposomes and surfactants but none have anticipated the combinations that we describe to modify the encapsulation state and/or release rate of the encapsulated drug and none describe the addition of the surfactant to a pre-existing liposome formulation. For example, an issued patent, U.S. Pat. No. 7,923,029 describes spray-freeze-dried formulations for pulmonary administration. The focus of this patent is on spray-freeze drying the formulation to preserve stability, but does not anticipate the possibility of mixing a surfactant with a pre-existing liposomal formulation to alter the drug encapsulation state and/or its release profile.

Another issued patent, U.S. Pat. No. 7,749,485 describes a liposome assembly for therapeutic and/or diagnostic use. The assembly comprises a liposome and a plurality of micellar components associated thereto, said micellar components being associated to the outer surface of the envelope of said liposome through a substantially electrostatic interaction and the active compound incorporated into the micelles, not within the liposomes. The focus of this patent is on liposomes associated with micelles to increase the residence time of said liposome in the blood stream but does not anticipate the use of surfactant to alter the encapsulation state of the liposome and/or the drug release profile.

Another issued patent, U.S. Pat. No. 7,368,129 describes a structural class of amphiphilic molecules which incorporate a hydrophilic material or polymer attached, at spatially distinct sites, to at least two hydrophobic residues. However, the inventors require covalent attachment of the surfactants while in our invention the surfactant is mixed with the liposomes without the need for covalent attachment to modify the encapsulation state and/or release rate of drug from the liposomes.

U.S. Pat. No. 7,033,574 describes stable microbubble suspensions which can be made from liposomes or surfactants but does not anticipate the use of both together and does not describe compositions to modify the drug encapsulation state and/or its release profile.

Another patent, U.S. Pat. No. 6,767,554 describes complexes of cationic liposomes and polydeoxribonucleotides. Our invention describes the use of surfactants to modify the encapsulation state and release rate of encapsulated drugs whereas this patent uses cationic liposomes as a means to complex with the nucleic acids which are located on the surface of the liposomes. The nucleic acids were never encapsulated in the liposomes. So this patent does not anticipate the use of surfactants to modify the encapsulation state and release rate of encapsulated drugs including encapsulated nucleic acids.

U.S. Pat. No. 6,296,870 describes liposomes comprised of phospholipids, cholesterol, an active agent associated with the lipid bilayer (versus being encapsulated within the interior aqueous milieu of the liposomes) and specific surfactants contained within the lipid bilayer which result in higher concentrations of the active agent to be incorporated into the bilayer. Other related patents, U.S. Pat. Nos. 5,882,679, 5,827,533 and 6,143,321 describes liposomes with entrapped surfactant micelles within the liposome vesicle. These patents do not cover drugs encapsulated within the interior of the liposome nor do they anticipate the use of surfactants to modulate the encapsulation state and/or release profile of an encapsulated drug.

U.S. Pat. No. 5,902,604 describes the addition of small amounts of surfactant in a lyophilized pre-liposome formulation of a lipophilic drug to aid in reconstitution. They did not anticipate the benefit of adding surfactant to a preexisting liposome formulation containing an encapsulated drug to modulate the encapsulation state and/or release rate of the drug.

U.S. Pat. No. 5,328,628 describes a method to lyse liposomes by the addition of anionic surfactants to the liposomes. This is in contrast to our invention for which the liposomes retain their structure but the encapsulation state and release rate can be modified.

U.S. Pat. No. 5,019,394 describes liposomes for which high Krafft point anionic surfactants are components of the liposomal membrane. This is in contrast to our invention for which the liposomes are preformed and the surfactant is subsequently added to the liposomes and the surfactant associates with the liposomes to modify the encapsulation state and/or drug release rate.

Liposome formulations of the invention may be administered concurrently with other drugs as described here. For example, the liposomes of the invention may be used along with drugs such as DNase, a mucolytic agent, chemicals that up-regulate the chloride ion channel or increase flow of ions across the epithelial surface of cells, a bronchodilator, a steroid, a P2Y2 agonist, an elastase inhibitor such as Alpha-1 antitrypsin (AAT), N-acetylcysteine, agents that enhance the activity of the antibiotic against biofilm bacteria such as sodium salicylate, interferon gamma, interferon alpha, bronchodilators, steroids, or a fluoroquinolone selected from the group consisting of amifloxacin, cinoxacin, ciprofloxacin, danofloxacin, difloxacin, enoxacin, enrofloxacin, fleroxacin, irloxacin, lomefloxacin, miloxacin, norfloxacin, ofloxacin, pefloxacin, rosoxacin, rufloxacin, sarafloxacin, sparfloxacin, temafloxacin and tosufloxacin or an antibiotic selected from the group of tobramycin, colistin, azithromycin, amikacin, cefaclor (Ceclor), aztreonam, amoxicillin, ceftazidime, cephalexin (Keflex), gentamicin, vancomycin, imipenem, doripenem, piperacillin, minocycline, or erythromycin.

The preceding merely illustrates the principles of the invention. It will be appreciated that those skilled in the art will be able to devise various arrangements which, although not explicitly described or shown herein, embody the principles of the invention and is included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Until now we have discussed primarily the application of this invention to treat infections in CF, non-CF bronchiectasis, and non-TB mycobacterial patients. However, it will be obvious to one skilled in the art that this invention will have utility and advantages beyond these indications. This method of treatment applies to other disease states which involve infections of the nasal passages, airways, inner ear, or lungs; including but not limited to: bronchiectasis, tuberculosis, pneumonia; including but not limited to ventilator associated pneumonia, community acquired pneumonia, bronchial pneumonia, lobar pneumonia; infections by *Streptococcus pneumoniae, Chlamydia, Mycoplasma pneumonia, staphylococci*, prophylactive treatment or prevention for conditions in which infection might arise, e.g., intubated or ventilated patients, infections in lung transplant patient, bronchitis, pertussis (whooping cough), inner ear infections, streptococal throat infections, inhalation anthrax, tularemia, or sinusitis.

EXAMPLE

The following examples are put forth so as to provide those of ordinary skill in the art with a complete disclosure and description of how to make and use the present invention, and are not intended to limit the scope of what the inventors regard as their invention nor is it intended to represent that the experiment below is the only experiment performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials

Free ciprofloxacin (FCI), 20 mg/ml is in an acetate-buffered aqueous formulation at pH 3.3 and Lipoquin, liposomal ciprofloxacin (CFI), 50 mg/ml is in a histidine-buffered aqueous formulation at pH 6.0. Donor Adult Bovine Serum was obtained from HyClone (Logan, Utah).

Preparation of Liposomal Ciprofloxacin

Lipoquin is an aqueous dispersion of unilamellar liposomes of ~80 nm containing hydrogenated soy phosphatidylcholine (HSPC) and cholesterol. The preparation of Lipoquin, liposomal ciprofloxacin (CFI), has been reported previously (Ong et al. 2012). Briefly, multilamellar liposomes are extruded through membranes to produce unilamellar liposomes which are then actively loaded with ciprofloxacin (Webb et al. 1998, Yim et al., 2006). Any unencapsulated ciprofloxacin is removed by diafiltration resulting in >99% encapsulated ciprofloxacin at a target concentration of 50 mg/ml ciprofloxacin. Pulmaquin, dual release ciprofloxacin for Inhalation (DRCFI), is an equivolume mixture of FCI and CFI resulting in ~70% encapsulated and ~30% free ciprofloxacin.

Addition of Surfactant to CFI

One series of experiments explored the use of various surfactants, including SPAN 20, SPAN 80, Pluronic L62, Pluronic L44, polysorbate 20 and polysorbate 80, to modify the properties of liposomal ciprofloxacin, CFI. In these studies the formulations contained 12.5 mg/ml CFI (i.e., diluted four-fold) in 0.01, 0.05, 0.1, 0.5 or 1% of each surfactant. In a second series of experiments utilizing only polysorbate 20, CFI, was diluted from 50 mg/ml to 30, 20, 15, 12.5 or 10 mg/ml with water and surfactant to achieve a final concentration of 0.1, 0.2, 0.4, 0.8, 1.2, 1.6 and 2.0% polysorbate 20. The samples in both sets of experiments were allowed to equilibrate for at least 30 min to provide adequate time for the surfactant to associate with the liposomes. No further change in the properties of these formulations was observed when samples were equilibrated for longer periods of time (data not shown). For the 12.5 mg/ml CFI containing polysorbate 20, an experiment was conducted to determine if the properties of these preparations depended upon the order of addition of water and surfactant to the CFI. In a separate experiment, after 30 min equilibration, the 30 mg/ml CFI preparations containing various levels of surfactant were diluted with water to 10 mg/ml CFI to determine the effect of dilution on the properties of the formulations. For some of these preparations, the vesicle size distribution, drug encapsulation state, cryo-TEM images and IVR profiles were determined Vesicle Size Each CFI sample was diluted with saline to a concentration of ~1 mg/ml CFI (2 mg/ml liposomes), and 0.5 ml was transferred to a disposable culture tube (Kimble Glass Inc., USA) for vesicle size analysis using a Submicron Particle Sizer Autodilute Model 370 (Nicomp, USA). The following instrument parameters were selected: temperature: 23° C.; viscosity: 0.933; refractive index: 1.333; intensity set point: 300 KHz; channel width: 10 μsec; scattering angle: 90; run time: 5 min; mode: vesicle; Gaussian distribution. The mean and standard deviation (SD) of the vesicle size distribution were recorded.

Drug Encapsulation

Nanosep centrifugation devices with membrane filters of 10,000 or 30,000 molecular weight cut-offs were used to separate free drug from liposomal encapsulated drug. Each sample was diluted tenfold into acetate buffer (50 mM sodium acetate, 145 nM NaCl, pH 4.0) and 400 μL was transferred to the centrifugation device and centrifuged for 18 min at 10,000 rpm (8,100 g). The filtrate, representing the free ciprofloxacin component, was analyzed by HPLC for ciprofloxacin content. The total amount of ciprofloxacin, representing both the encapsulated and free drug, was quantified by HPLC after diluting the CFI sample twenty-fold into 80% methanol to 'solubilize' the liposomes. The percent encapsulation was determined by comparing the free drug to the total drug in each sample.

Cryogenic Transmission Electron Microscopy (CryoTEM)

To obtain visual images of the liposome formulations, cryoTEM analysis was performed using a JEOL 2100 (Tokyo, Japan) instrument operated at 200 kV. The CFI samples were diluted to ~5 mg/ml (10 mg/ml liposomes) with water and 3 µL of each sample was applied to a glow discharge Quantifoil carbon grid (Jena, Germany) in a chamber controlled to 22° C. and 100% RH. Grids were blotted once with filter paper, at a blotting angle of 2 mm for 2 s, and vitrified by plunging into liquid ethane using a Vitrobot (F.E.I., Eindhoven, Netherlands). The vitrified samples were stored in liquid nitrogen prior to cryoTEM analysis.

In Vitro Release (IVR)

The IVR assay measures the release of encapsulated ciprofloxacin when incubated at 37° C. in 50% bovine serum. Briefly, the CFI samples were diluted to 50 µg/ml ciprofloxacin in HEPES Buffered Saline (HBS: 20 mM HEPES, 145 mM NaCl, pH 7.4) and mixed one-to-one with chilled (2-8° C.) bovine serum (Hyclone) and placed in a shaking water bath (Techne, TSBS40 (Staffordshire, UK)) at 37° C. and 150 rpm. Duplicate samples were removed periodically; e.g., 30, 60, 120 and 240 min, and placed in an ice-water bath to terminate any further release of encapsulated drug from the liposomes. The released ciprofloxacin was separated from the liposome-encapsulated ciprofloxacin by transferring 400 µL of each chilled sample to a Nanosep centrifugal device and centrifuging at 10,000 rpm for 18 min. The filtrate was removed for subsequent quantitation of the released ciprofloxacin by HPLC. This value was normalized by multiplying by 1.05, to correct for a small but reproducible loss of free drug in the filtration devices in the presence of serum (Cipolla et al., 2013, submitted). The original CFI sample was diluted into 80% methanol to dissolve the liposomes and allow for quantitation of the total amount of ciprofloxacin by HPLC. The percent release at each time point was calculated by comparing the free drug to the total drug.

High Performance Liquid Chromatography (HPLC)

The amount of ciprofloxacin in each sample was quantified using an HPLC method as described previously (Cipolla D C et al., 2010). Briefly, HPLC was performed using a Nucleosil C-18 column (5 µm, 4.6×150 mm, Canadian Life Science, CA) protected with a Nucleosil C-18 guard column (4×3.0 mm, Phenomenex, USA) both at 35° C. The mobile phase was a mixture of 0.5% TEA in water, pH 3.0 and 100% methanol (83:17 v/v) and the isocratic elution was performed at a flow rate of 0.9 ml/min Ciprofloxacin was detected and quantified at a wavelength of 277 nm.

Long Term Stability

Four liposomal ciprofloxacin formulations containing 12.5 mg/ml CFI, and 0.4% polysorbate 20, but differing in pH, were stored at refrigerated conditions for evaluation of long term stability. The unadjusted pH was 5.5, and the target values for the adjusted pH formulations were 5.2, 4.9 and 4.7. The pH was lowered in three of the samples by addition of various amounts of 25 mM acetate buffer, pH 4.0. Fifty ml of each formulation was prepared and ~6 ml aliquots were pipetted into eight 10 ml glass vials and stored at 2-8° C. until use. At various time points, including initial, one month, ten weeks, 6 months and 1 year, vials were removed for analysis of their appearance, pH, vesicle size distribution, drug encapsulation, and IVR profile. The aerosol properties were determined at the initial, one month, and six month time points.

Aerosol Characterization

The aerosol particle size distribution of the 12.5 mg/ml CFI formulation containing 0.4% polysorbate 20, pH 5.5 was determined using laser diffraction (HELOS/BF, Sympatec GmbH, Clausthal-Zellerfeld, Germany). The aerosol output was drawn at 12.5 L/min through a flow-through cell in front of the optical lens and twenty time slices of 500 µsec each were analyzed. WINDOX 5 software was used assuming a shape factor of 1.00, density of 1.019 g/cm3, and Mie analysis mode to calculate a volume mean diameter (VMD) and geometric standard deviation (GSD).

At the initial time point, 5 ml aliquots of the control CFI formulation and the pH 5.5, 4.9 and 4.7 CFI formulations containing 0.4% polysorbate 20 were loaded into the Pari eFlow® rapid nebulizer reservoir (Pari Pharma, Stamberg, Germany) with a 4 µm mesh, the nebulizer was turned on and the aerosol output was collected in a SKC BioSampler (USA) containing 5 ml of 25 mM acetate buffer, pH 4.0. The nebulization time and mass of liposomal ciprofloxacin in the nebulizer residual and collected aerosol compartments were determined in each of duplicate experiments. The mean vesicle size and state of encapsulation were recorded before nebulization and after nebulization for the formulation recovered in the nebulizer reservoir and the collected aerosol. In subsequent characterization experiments at the 1 month and 6 month time points, the aerosol evaluation was performed on the accumulated formulation in the device mouthpiece which represented impaction of droplets that had passed through the mesh. This was done to avoid possible liposome disruption during collection in the Bio-Sampler. For the 1 and 6 month time points, both the vesicle size and encapsulation state were measured. The IVR profiles were also characterized at the 6 month time point only.

Results

Interaction of Surfactants with Liposomal Ciprofloxacin

Upon addition of surfactant to liposomal ciprofloxacin (CFI) at a final concentration of 12.5 mg/ml, in a hypotonic environment due to the dilution with water, all surfactants caused some release of encapsulated ciprofloxacin with the amount released increasing with increasing surfactant concentration (FIG. 1). The release of encapsulated drug happened very rapidly, well within 30 min, and no further release was observed thereafter (see section on long term stability). However, the amount of drug that was released was very dependent on the choice of surfactant, with both polysorbate 20 and polysorbate 80 resulting in substantial release of ciprofloxacin while none of the other surfactants that were tested produced more than 1-2% release of encapsulated drug over the surfactant concentration ranges that were evaluated (FIG. 1). The mean vesicle size of CFI was unchanged in the presence of either pluronic L44 or pluronic L62, increased by 1 to 3 nm for SPAN 20, SPAN 80, and polysorbate 20, and increased by up to 8 nm for polysorbate 80 (Table I). All of the surfactants investigated caused some increase in the amount of free drug.

Figure 2A:
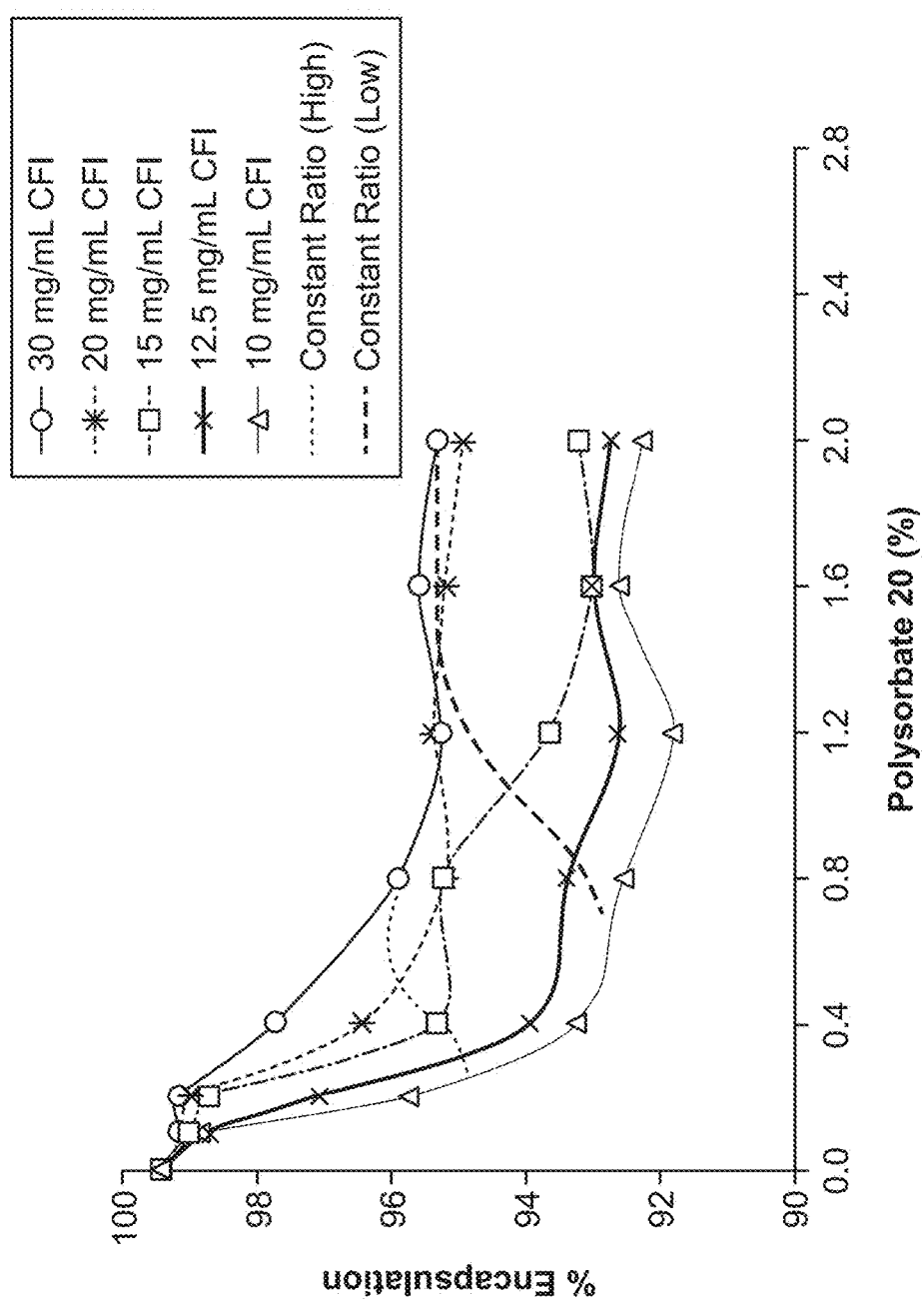
FIG. 2A is a graph showing the effect of addition of polysorbate 20 on the state of encapsulation of CFI. CFI at 50 mg/ml ciprofloxacin was diluted to a final concentration of 30, 20, 15, 12.5 and 10 mg/ml with isotonic histidine buffer in sodium chloride and then either an aliquot of 1% or 10% polysorbate 20 to achieve a final surfactant concentration of 0.1, 0.2, 0.4, 0.8, 1.2, 1.6 or 2.0%. The dotted black lines represent a constant ratio of surfactant to liposomes.

In the next series of experiments, the effect of changing both the CFI and surfactant (polysorbate 20) concentrations was investigated, either using isotonic histidine buffer, or water, as the dilution medium. Using isotonic histidine buffer as the dilution medium, there was much less effect of addition of surfactant on the encapsulation state of CFI (FIG. 2A).

Figure 2B:
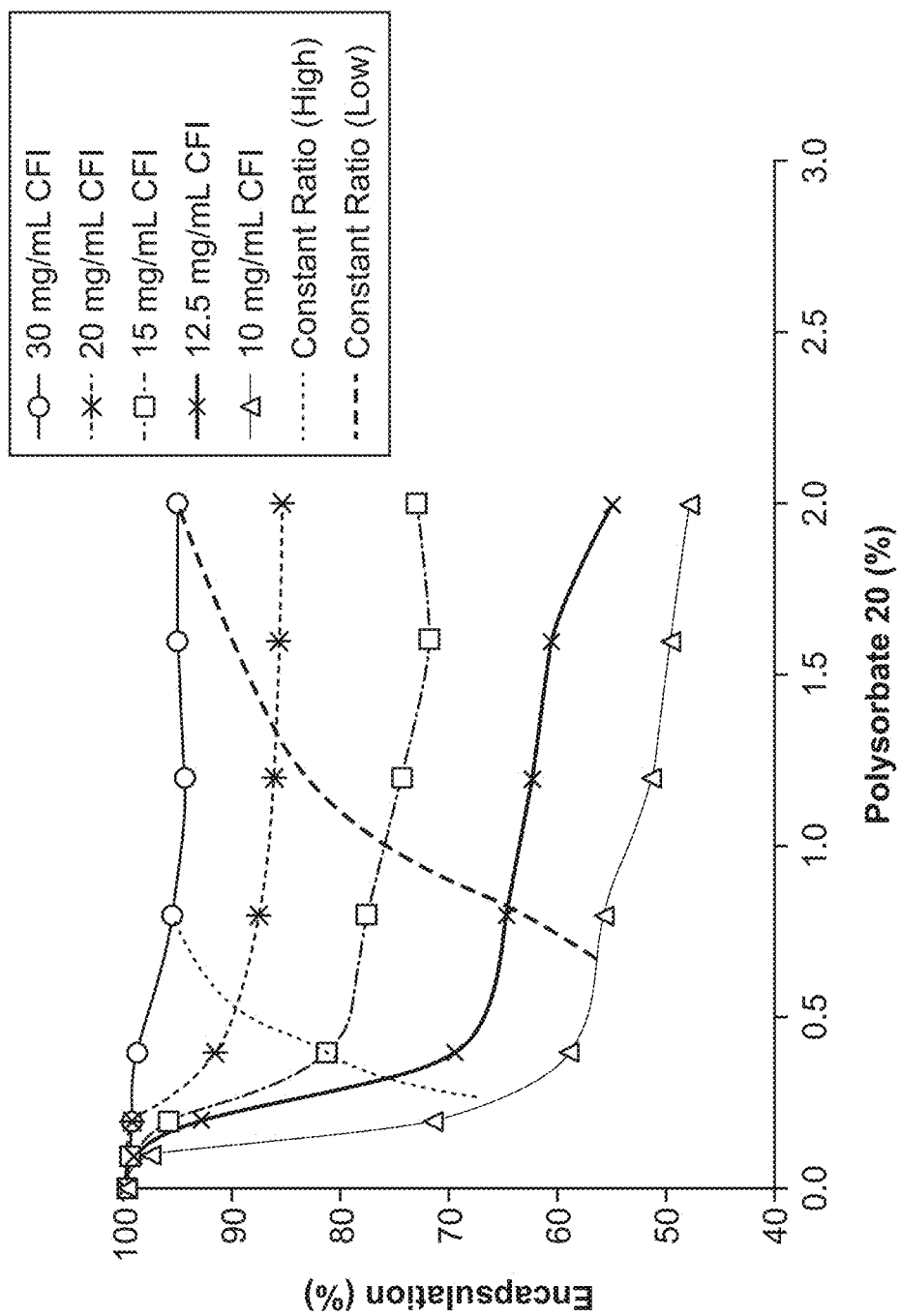
FIG. 2B is a graph showing the effect of addition of polysorbate 20 on the state of encapsulation of CFI. CFI at 50 mg/ml ciprofloxacin was diluted to a final concentration of 30, 20, 15, 12.5 and 10 mg/ml with water and then either an aliquot of 1% or 10% polysorbate 20 to achieve a final surfactant concentration of 0.1, 0.2, 0.4, 0.8, 1.2, 1.6 or 2.0%. The dotted black lines represent a constant ratio of surfactant to liposomes.
Figure 2C:
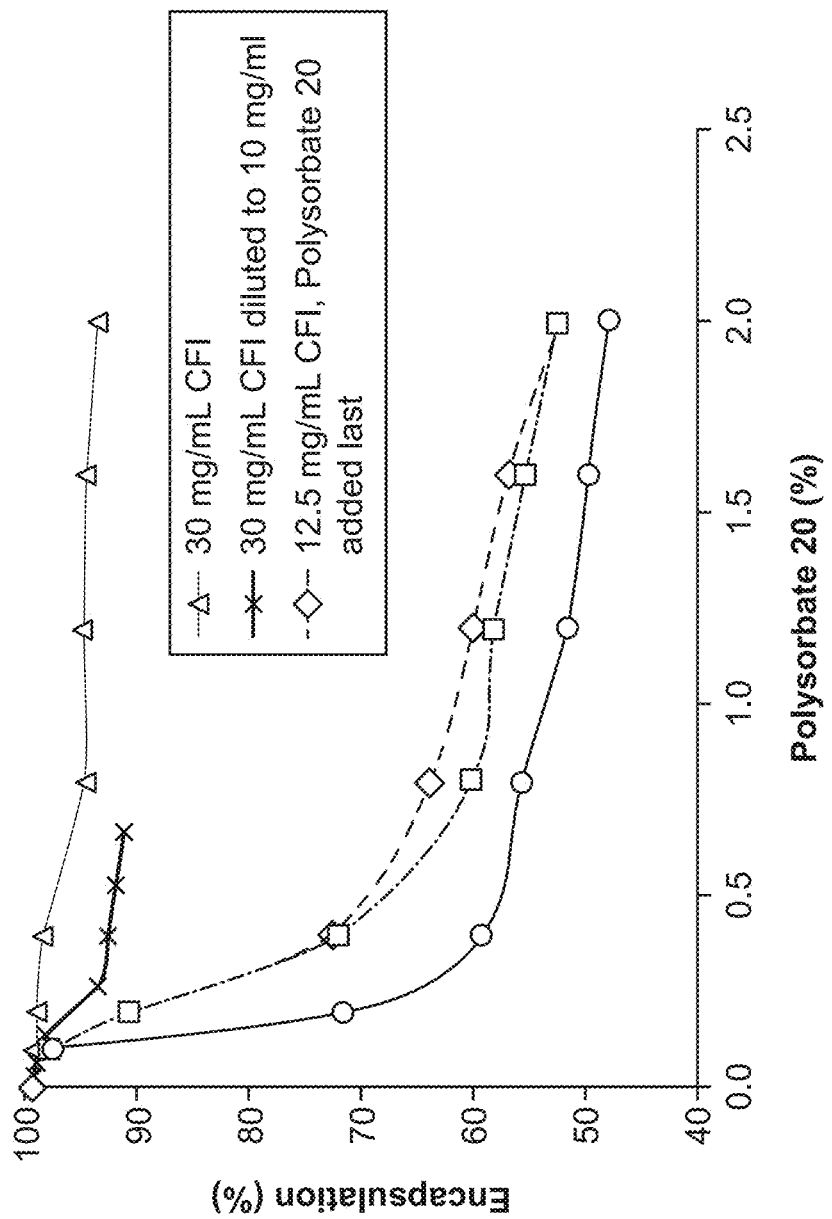
FIG. 2C is a graph similar to 2B with CFI at 30 mg/ml and 0.1, 0.2, 0.4, 0.8, 1.2, 1.6 or 2.0% polysorbate 20 was diluted to a final concentration of 10 mg/mL with water to achieve a final concentration of 0.03, 0.07, 0.13, 0.27, 0.4, 0.53 and 0.67% polysorbate 20. In a separate experiment, CFI at 50 mg/ml ciprofloxacin was diluted to a final concentration of 12.5 mg/ml with water and 1% or 10% polysorbate 20 to achieve a final surfactant concentration of 0.1, 0.2, 0.4, 0.8, 1.2, 1.6 or 2.0%. In one experiment the water was added to the CFI before the polysorbate 20 and in the other the polysorbate 20 was added to the CFI before the water.

However, under identical conditions except using water as the dilution medium there was a dramatic difference in the encapsulation state. For any given concentration of polysorbate 20, there was a greater extent of release of encapsulated ciprofloxacin for more dilute CFI formulations in the hypotonic environment than for more concentrated CFI formulations (FIG. 2B). Across this three-fold range in CFI concentration, for a constant ratio of surfactant to liposomes, there was not a comparable percentage release of ciprofloxacin (dotted lines in FIG. 2B). Instead, for the 30 mg/ml CFI formulation, the encapsulation state was ~95% while it decreased to ~56% for 10 mg/ml CFI. In another experiment, the encapsulation state of 30 mg/ml CFI in a range of polysorbate 20 concentrations was measured after 30 min equilibration, and then was re-measured after dilution with water to 10 mg/ml CFI (FIG. 2C). While there was a decrease in encapsulation upon the three-fold dilution, the decrease was relatively small compared to when the 10 mg/ml CFI formulation was prepared directly from the 50 mg/ml CFI by addition of surfactant. In a final experiment shown on the same graph, the order of dilution was evaluated by adding the surfactant to the 50 mg/ml CFI before immediate dilution with water or immediately after dilution with water. In this case there was little difference in the encapsulation state between the two preparations (FIG. 2C).

Cryo-TEM 12.5 mg/ml CFI samples with and without various levels of polysorbate 20 were imaged by cryoTEM. The CFI formulation without surfactant was comprised of spherical, unilamellar liposomes between approximately 50 and 100 nm in size (FIG. 3A). CFI samples containing 0.05% polysorbate 20 (FIG. 3B), 0.2% polysorbate 20 (FIG. 3C), and 0.4% polysorbate 20 (FIG. 3D) all appeared to be qualitatively similar to CFI with respect to liposome size and lamellarity. However, with increasing concentration of polysorbate 20, there was a greater proportion of liposomes that were lighter in shading suggesting a loss of encapsulated ciprofloxacin (FIG. 3D). There were also a very small fraction of disk-like fragments which may represent pieces of ruptured liposomes (FIG. 3D). To determine if the lighter density liposomes are consistent with loss of encapsulated drug, empty liposomes and a 50:50 mixture of empty liposomes and CFI were also imaged (FIGS. 3E and 3F). The empty liposomes were comparable to CFI in terms of size and lamellarity, but had lighter density (FIG. 3E). The 1:1 mixture of the empty liposomes and CFI revealed a mosaic of liposomes with both light and dark shading in approximately equal proportion (FIG. 3F). These results suggest that the addition of increasing amounts of polysorbate 20 up to 0.4% caused leakage of ciprofloxacin from a subset of liposomes which retained their physical integrity after loss of encapsulated drug.

IVR Profile

The IVR assay measures the release of encapsulated ciprofloxacin from the liposomes after incubation with bovine serum at 37° C. Consistent with the encapsulation assay data (FIG. 2), the time zero release values in the IVR assay (FIG. 4A) represent the state of encapsulation before incubation with the release agent. For the control CFI vial, the time zero release value is ~1%. For DRCFI, which is a mixture of approximately 70% CFI and 30% free ciprofloxacin, the time zero value is ~30%. For the 12.5 mg/ml CFI containing various levels of surfactant, the amount of free ciprofloxacin increased with increasing polysorbate 20 from ~2% for 0.05% polysorbate 20 to ~27% for 0.4% polysorbate 20. By the last time point at 4 hours, all of the formulations reached a plateau value in the IVR assay representing ~100% release of encapsulated ciprofloxacin.

The IVR profiles for the CFI formulations containing 0.05, and 0.1% polysorbate 20 were very similar to that for CFI alone. However, the IVR profile for the CFI formulation containing 0.4% polysorbate 20 had marked differences to that for CFI. The $T_{30\ min}$ value is an approximate representation of the 'midpoint' of release for CFI (Cipolla et al., 2013, submitted). The $T_{30\ min}$ values increased with increasing polysorbate 20, from ~44% for CFI alone to ~66% for CFI containing 0.4% polysorbate 20. However, one cannot directly compare the $T_{30\ min}$ values of these formulations to assess changes to the release rates because the encapsulation states at the start were not equivalent. To address this issue one can 'normalize' the $T_{30\ min}$ values by subtracting the initial value ($T_{0\ min}$) and dividing by the total available range of release ($T_{240\ min}-T_{0\ min}$) and converting to a percentage. The normalized $T_{30\ min}$ values are 44.4% for CFI, and 43.4%, 46.8%, 47.6% and 55.7% for CFI containing 0.05, 0.1, 0.2 and 0.4% polysorbate 20, respectively. The release of encapsulated ciprofloxacin was faster from the 12.5 mg/ml liposome formulation containing 0.4% polysorbate 20 than for CFI without added surfactant. In addition, while CFI containing 0.4% polysorbate 20 had a comparable initial release value to that for DRCFI, 27% versus 30%, respectively, its release rate was faster than DRCFI with a $T_{30\ min}$ value of 66%, versus 57%, respectively. One may question whether the surfactant has altered the membrane permeability of the liposomes and thus their release profile, or instead, whether the surfactant is simply operating like serum, as a release vehicle itself. To test that hypothesis, control CFI was diluted into the release vehicle (serum) with or without polysorbate 20 and the IVR assay was repeated. The concentration of surfactant in the IVR assay in that experiment (0.0008%) was identical to that for 12.5 mg/ml CFI containing 0.4% polysorbate 20 after the 500-fold dilution into the IVR assay buffer. There was no effect of the surfactant on the IVR profile (data not shown).

Long Term Stability

Because ciprofloxacin is poorly soluble near neutral pH, the 12.5 mg/ml CFI formulation containing 0.4% polysorbate 20 which resulted in release of ~25 to 30% ciprofloxacin was not expected to possess good long term stability. In fact, rod-shaped crystals of ciprofloxacin were observed external to the liposomes under light microscope within 48 h of addition of the surfactant when the pH was not adjusted (data not shown). In order to develop a formulation with acceptable long term stability, the external pH of the 12.5 mg/ml CFI containing 0.4% polysorbate 20 was reduced from pH 5.5, for the unmodified formulation, to pH 5.2, 4.9 and 4.7 with addition of pH 4.0 sodium acetate buffer. These formulations were stored refrigerated for periodic evaluation of appearance, vesicle size distribution, ciprofloxacin encapsulation, pH and IVR profile. The visual appearance of the pH 4.7 and 4.9 CFI formulations containing 0.4% polysorbate 20 remained particle-free throughout the one year study while a small number of fine particles were observed in the pH 5.2 formulation at the 2.5, 6 and 12 month time points. The mean liposome vesicle size ranged between 90 to 97 nm across all four formulations with the lowest pH formulation having a slightly larger mean vesicle size than the others (Table II). There was no meaningful change in vesicle size for any formulation during the one-year study. The encapsulation of the CFI control sample remained at ~99% for the one-year study (Table III). While the 12.5 mg/ml CFI formulation at pH 5.5 containing 0.4% polysorbate 20 had 70-75% drug encapsulation, the percent encapsulation increased to ~80, ~85 and ~92% when the pH was lowered to 5.2, 4.9 and 4.7, respectively (Table III). These encapsulation values remained fairly constant over the one-year refrigerated storage period. The pH was unchanged for the pH 4.7 and 4.9 CFI formulations containing 0.4% polysorbate 20 throughout the one-year study but decreased slightly for the pH 5.2 formulation at the 6 and 12 month time points (Table IV).

The IVR profiles of these three formulations show similar characteristics to that for the formulation without pH modification (FIG. 4B). However, the T=0 release value decreased with decreasing pH from ~27% for the sample with unmodified pH to ~12% at pH 4.7. The T=0 release values are comparable to the encapsulation values reported in Table III. The release profiles for the formulations containing 0.4% polysorbate 20 were comparable, but faster than for CFI without 0.4% polysorbate 20, except for the pH 4.7 formulation which released most of its contents within the first 30 min. The IVR profiles for the pH 5.2, 4.9 and 4.7 CFI formulations containing 0.4% polysorbate 20 were assayed after refrigerated storage for 6 months (FIG. 4C) and 1 year (FIG. 4D). The IVR profiles for the CFI formulations containing 0.4% polysorbate 20 at pH 5.2, 4.9 and 4.7 were unchanged over this one-year time frame.

Aerosol Characterization

Initially, CFI formulations containing 0.4% polysorbate 20 were evaluated using various jet nebulizers to characterize their aerosol performance. The presence of the surfactant resulted in excessive foaming and led to very low and inconsistent aerosol output rates thus rendering jet nebulization inappropriate for use with these formulations. A transition to a vibrating mesh nebulizer, the PARI eFlow rapid, was then made. Using this device, 5 mL of each formulation was nebulized in 3.4 to 4.0 min, slightly faster than that for the CFI control without surfactant (Table V). The emitted dose (ED) values for the three experimental formulations ranged between 57 to 61% of the dose loaded in the nebulizer, lower than the ~72% ED observed for the CFI Control (Table V). Given the faster nebulization times, it makes sense that the ED values would be lower for the experimental formulations: the lower ED values for the experimental formulations were likely a result of the small amount of foam observed in the reservoirs which would have reduced the formulation volume available to pass through the mesh. The mass balance recovery exceeded 90% on average. For all three experimental formulations, the mean vesicle size increased by ~3 nm for the material recovered from the nebulizer reservoir and by an additional ~30 nm for the collected aerosol (Table V). This is in contrast to the control CFI formulation for which there was no significant change in mean vesicle size for either the nebulizer reservoir or collected aerosol compartments (Table V). The encapsulation of ciprofloxacin recovered from the nebulizer reservoir decreased significantly for all three formulations to between 65 to 77% whereas the encapsulation state in the control CFI formulation was unchanged (Table V).

At the 1 month time point, the CFI formulations containing 0.4% polysorbate 20 at pH 5.2, 4.9 and 4.7 were aerosolized but this time, instead of collecting the aerosol in the BioSampler for analysis, aerosol droplets which coalesced inside the mouthpiece were evaluated for vesicle size and encapsulation state. This change was made in case the BioSampler collection process was contributing to changes in the state of the sample which could account for the increase in vesicle size observed in the aerosol samples at the initial time point. For all three formulations, there was a small increase in the average vesicle size for the residual solution in the nebulizer reservoir, consistent with the initial assessment (Table VI). However, in contrast to the previous results at time zero, there was no additional increase in the vesicle size for the collected aerosol samples for all three formulations (Table VI). The encapsulation state for the formulation remaining in the nebulizer reservoir did not decrease as significantly for any of the three formulations as at the time zero analysis. However, the collected aerosol samples all decreased to an encapsulation state of between 70 to 80%, consistent with what was observed at time zero (Table VI).

At the 6 month time point, the effect of aerosolization of the CFI formulations containing 0.4% polysorbate 20 at pH 5.2, 4.9 and 4.7 was evaluated with respect to vesicle size, encapsulation state and IVR profile. For all three formulations, the mean vesicle size increased by 2-3 nm for the sample recovered from the nebulizer reservoir and by a further 1-3 nm for the collected aerosol sample in the mouthpiece (Table VI), consistent with what was observed for the one month time point. The encapsulation state decreased slightly by 1 to 6% for all three formulations whether recovered from the nebulizer reservoir or after aerosolization (Table VI). For all three formulations, the IVR profiles of the collected aerosol samples were comparable to those for the residual formulation remaining in the nebulizer reservoir (FIG. 4E). The IVR profiles for the aerosolized pH 5.2 and 4.9 CFI formulations containing 0.4% polysorbate 20 were also comparable to that for the unnebulized control samples (FIG. 4D). However, for the pH 4.7 CFI formulation containing 0.4% polysorbate 20, the IVR profiles for both the collected aerosol and nebulizer reservoir samples (FIG. 4E) did not show the rapid release behavior observed for the unnebulized control (FIG. 4D), but instead had IVR profiles that were similar to the formulations at higher pH.

Figure 3A:
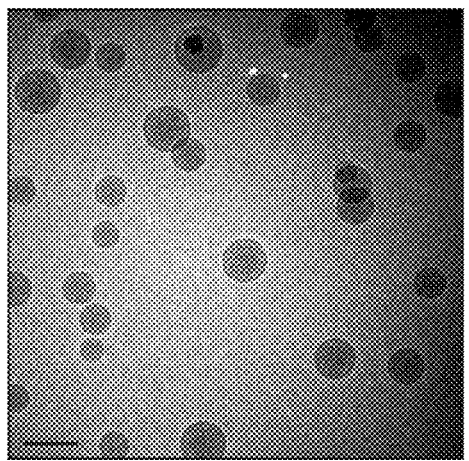
FIG. 3 includes seven micrograph images as images 3A, 3B, 3C, 3D, 3E, 3F and 3G are CryoTEM micrographs of various preparations of liposomal ciprofloxacin. The scale bar in the bottom left-hand corner of each micrograph is 100 nm for 3A, 3D, 3E, 3F and 3G and 200 nm for 3B and 3C. All samples were applied at a concentration of ~10 mg/mL liposomes. (A) 12.5 mg/ml CFI; (B) 12.5 mg/ml CFI in 0.05% polysorbate 20; (C) 12.5 mg/ml CFI in 0.2% polysorbate 20; (D) 12.5 mg/ml CFI in 0.4% polysorbate 20; (E) empty liposomes; (F) 1:1 mixture of empty liposomes and CFI; (G) 12.5 mg/ml CFI in 0.4% polysorbate 20 after mesh nebulization.
Figure 3B:
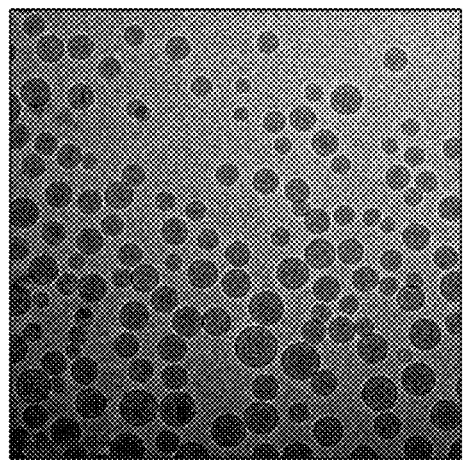
Figure 3C:
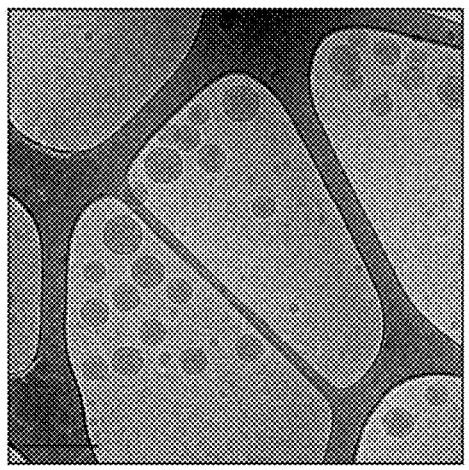
Figure 3D:
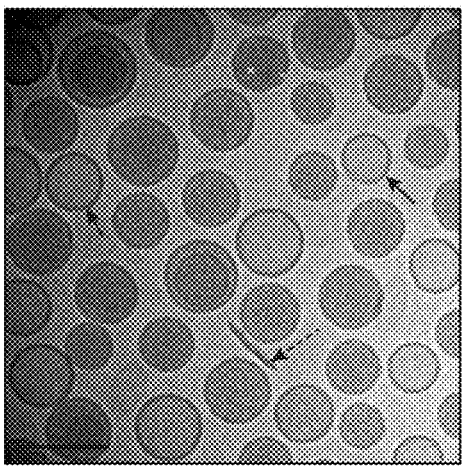
Figure 3E:
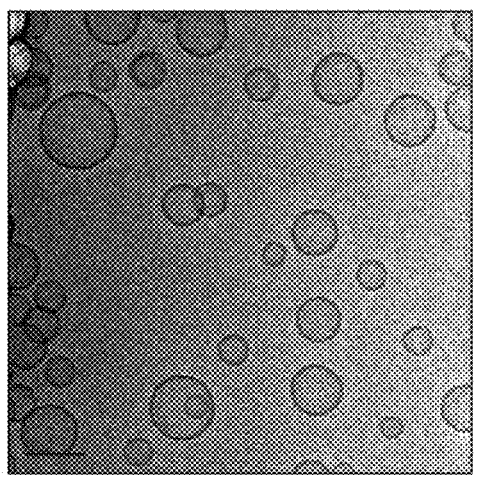
Figure 3F:
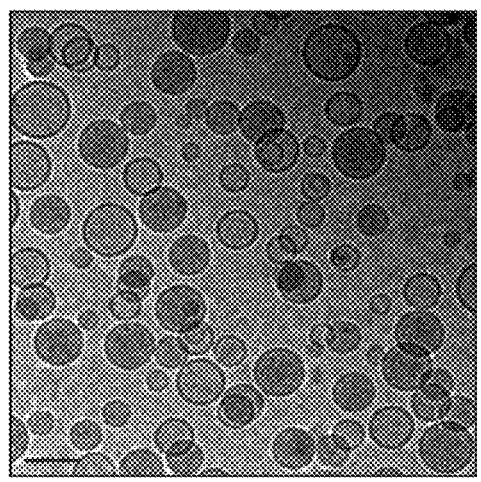
Figure 3G:
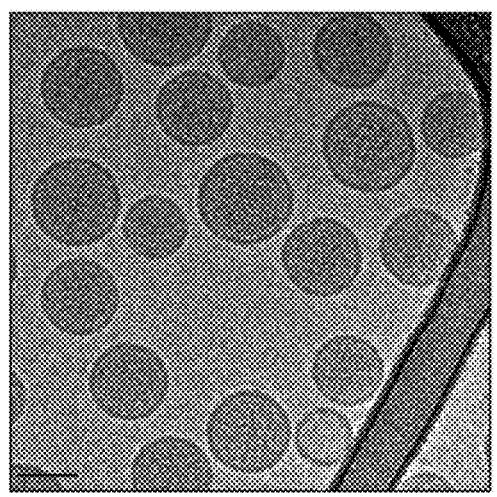

The aerosol particle size distribution of the 12.5 mg/ml CFI preparation containing 0.4% polysorbate 20 following mesh nebulization had VMD=3.74 μm (SD=0.01 μm, n=3) and a GSD=1.72 (SD=0.02, n=3). After exposure of the 12.5 mg/ml CFI formulation containing 0.4% polysorbate 20 to the mesh nebulization process, the aerosol sample recovered in the mouthpiece was not compromised with respect to the liposome structure or integrity by cryo-TEM analysis (FIG. 3G). There was no noticeable change compared to unnebulized samples in the size distribution of the liposomes or an increase in the proportion of liposome disk-like fragments or liposomes with lighter shading.

TABLES

TABLE I

The vesicle size distribution for 12.5 mg/mL CFI in the presence of the following surfactants: pluronic L44, pluronic L62, SPAN 20, SPAN 80, polysorbate 20 and polysorbate 80. Vesicle size data are reported as the mean (in nm) and [SD].

| Surfactant (%) | SPAN 80 | SPAN 20 | Pluronic L62 | Polysorbate 80 | Pluronic L44 | Polysorbate 20 |
|---|---|---|---|---|---|---|
| 0 | | | 93.5 [26.0] | | | |
| 0.01 | 93.4 [26.0] | 93.7 [27.6] | 93.4 [27.6] | 93.8 [29.0] | 94.7 [34.8] | 92.0 [30.6] |
| 0.05 | 93.5 [26.5] | 94.2 [28.9] | 93.4 [26.5] | 94.0 [24.9] | 94.6 [30.4] | 93.4 [30.8] |

TABLE I-continued

The vesicle size distribution for 12.5 mg/mL CFI in the presence of the following surfactants: pluronic L44, pluronic L62, SPAN 20, SPAN 80, polysorbate 20 and polysorbate 80. Vesicle size data are reported as the mean (in nm) and [SD].

| Surfactant (%) | SPAN 80 | SPAN 20 | Pluronic L62 | Polysorbate 80 | Pluronic L44 | Polysorbate 20 |
|---|---|---|---|---|---|---|
| 0.1 | 93.8 [28.2] | 94.7 [29.9] | 93.0 [25.2] | 97.9 [29.2] | 94.6 [30.3] | 93.9 [30.7] |
| 0.5 | 94.2 [34.0] | ND* | ND | 101.3 [33.8] | 94.7 [31.4] | 95.2 [31.9] |
| 1.0 | 96.7 [37.4] | ND* | 93.8 [24.0] | 101.6 [26.9] | 94.3 [34.0] | 94.6 [27.4] |

ND: Not done
*Preparation did not form a miscible solution.

TABLE II

The vesicle size distribution of the CFI Control and the pH adjusted 12.5 mg/ml CFI formulations containing 0.4% polysorbate 20 after refrigerated storage for 2.5, 6 and 12 months. Vesicle size data are reported as the mean (in nm) and [SD].

| Time (months) | CFI Control | pH 5.2 | pH 4.9 | pH 4.7 |
|---|---|---|---|---|
| 0 | 90.5 [25.7] | 90.6 [17.6] | 91.8 [25.8] | 93.4 [19.1] |
| 2.5 | 90.3 [24.7] | 93.6 [20.3] | 93.9 [15.6] | 95.2 [26.0] |
| 6 | 90.8 [20.5] | 93.6 [21.1] | 94.1 [24.0] | 96.5 [27.0] |
| 12 | 94.1 [27.8] | 94.3 [27.1] | 93.7 [22.5] | 95.6 [26.5] |

TABLE III

The percent encapsulation of ciprofloxacin of the CFI Control and the pH adjusted 12.5 mg/ml CFI formulations containing 0.4% polysorbate 20 after refrigerated storage for 1, 2.5, 6 and 12 months.

| Time (months) | CFI Control | pH 5.2 | pH 4.9 | pH 4.7 |
|---|---|---|---|---|
| 0 | 99.5 | 80.1 | 84.9 | 92.8 |
| 1 | 98.9 | 77.0 | 84.7 | 91.1 |
| 2.5 | 99.6 | 79.0 | 86.6 | 94.8 |
| 6 | 99.1 | 76.5 | 81.2 | 89.6 |
| 12 | 99.7 | 80.0 | 86.9 | 92.2 |

TABLE IV

The pH of ciprofloxacin of the CFI Control and the pH adjusted 12.5 mg/ml CFI formulations containing 0.4% polysorbate 20 after refrigerated storage for 1, 6 and 12 months.

| Time (months) | pH 5.2 CFI | pH 4.9 CFI | pH 4.7 CFI |
|---|---|---|---|
| 0 | 5.18 | 4.91 | 4.67 |
| 1 | 5.14 | 4.89 | 4.63 |
| 6 | 4.88 | 4.82 | 4.61 |
| 12 | 5.05 | 4.93 | 4.71 |

TABLE V

Characterization of the effect of nebulization of the CFI Control and pH adjusted 12.5 mg/ml CFI formulations containing 0.4% polysorbate 20. The vesicle size data are reported as the mean (in nm) and [SD]. The state of ciprofloxacin encapsulation is reported in terms of percentage. The percent recovery of ciprofloxacin in the nebulizer reservoir and in the collected aerosol (emitted dose) allows for a calculation of the mass balance. The nebulization time is recorded in min.

| Formulation | Expt. Run | Mean Vesicle Size (nm) Before Neb. | Neb. Res. | Aerosol | Encapsulation (%) Before Neb. | Neb. Res. | Recovery (%) Neb. Res. | Aerosol |
|---|---|---|---|---|---|---|---|---|
| CFI Control | #1 | 90.5 | 91.6 | 91.3 | 99.5 | 98.9 | 21.6 | 73.2 |
|  | #2 |  | 89.9 | 90.8 |  | 99.0 | 23.6 | 71.2 |
| pH 5.5 CFI | #1 | 90.6 | 92.1 | 127.9 | 70.2 | 67.6 | 34.9 | 58.2 |
|  | #2 |  | 94.7 | 135.0 |  | 65.6 | 33.2 | 60.3 |
| pH 5.2 CFI | ND | ND | ND | ND | 80.1 | ND | ND | ND |
| pH 4.9 CFI | #1 | 91.8 | 94.8 | 128.7 | 84.9 | 70.5 | 30.5 | 61.0 |
|  | #2 |  | 94.6 | 125.3 |  | 73.4 | 33.8 | 57.2 |
| pH 4.7 CFI | #1 | 93.4 | 96.2 | 125.9 | 92.8 | 77.0 | 30.6 | 59.1 |
|  | #2 |  | 96.3 | 123.1 |  | 73.7 | 33.3 | 59.5 |

TABLE VI

The liposome vesicle size distribution and the percent encapsulation of ciprofloxacin after 1 and 6 months refrigerated storage and following nebulization for the pH adjusted 12.5 mg/ml CFI formulations containing 0.4% polysorbate 20. Vesicle Size data are reported as the mean (in nm) and [SD]. Duplicate nebulization experiments were performed at the one month time point versus single experiments at the six month time point.

| Formulation | Expt. Run | Mean Vesicle Size (nm) [SD] | | | Encapsulation (%) | | |
|---|---|---|---|---|---|---|---|
| | | Before Neb. | Neb. Res. | Aerosol | Before Neb. | Neb. Res. | Aerosol |
| One Month Analysis | | | | | | | |
| pH 5.2 CFI | #1 | 91.1 [19.7] | 90.8 [24.2] | 92.6 [32.0] | 76.6 | 76.6 | 74.8 |
| | #2 | | 95.2 [16.7] | 95.8 [32.2] | | 77.0 | 73.1 |
| pH 4.9 CFI | #1 | 91.8 [25.3] | 93.0 [24.4] | 93.1 [33.7] | 85.2 | 82.8 | 73.4 |
| | #2 | | 94.1 [26.9] | 94.7 [29.7] | | 82.4 | 79.0 |
| pH 4.7 CFI | #1 | 95.4 [27.4] | 96.7 [23.6] | 96.2 [27.9] | 92.6 | 89.8 | 71.7 |
| | #2 | | 99.3 [27.5] | 99.7 [30.8] | | 89.1 | 81.2 |
| Six Month Analysis | | | | | | | |
| pH 5.2 CFI | | 93.6 [21.1] | 96.0 [23.8] | 99.0 [29.2] | 76.5 | 70.7 | 76.5 |
| pH 4.9 CFI | | 94.1 [24.0] | 96.5 [24.7] | 97.6 [29.8] | 81.2 | 75.7 | 77.2 |
| pH 4.7 CFI | | 96.5 [27.0] | 98.6 [23.1] | 101.2 [34.2] | 89.6 | 85.4 | 84.9 |

DISCUSSION

We have investigated the interaction of surfactants with a liposomal ciprofloxacin formulation with the goal to develop novel formulations with modified encapsulation states and release properties. Our strategy was to use sub-lytic quantities of surfactant, below the level that solubilizes the liposomes, so that the liposome vesicles retain their integrity, but may have altered drug release rates (Ruiz, et al. 1988, Memoli, et al. 1999). All of the surfactants resulted in some loss of encapsulated drug when mixed with CFI; the amount of released drug increased with addition of greater concentrations of surfactant (FIG. 1). These experiments were all done in a hypotonic environment, which may promote osmotic swelling of the liposomes, and thus enhance the ability of the surfactant to interact with the liposomes.

The new formulations of liposomes maintain their structural integrity for prolonged time periods as was observed in our one-year stability study. The cryo-TEM micrographs of mixtures of CFI and low levels of polysorbate 20 are practically indistinguishable from CFI alone (FIGS. 3A-3C). All three micrographs show predominantly circular, unilamellar liposomes around 50 to 100 nm in diameter. For low concentrations of polysorbate 20, up to 0.2%, there also did not appear to be a meaningful effect on the IVR release rate for 12.5 mg/ml CFI (FIG. 4A).

Figure 4A:
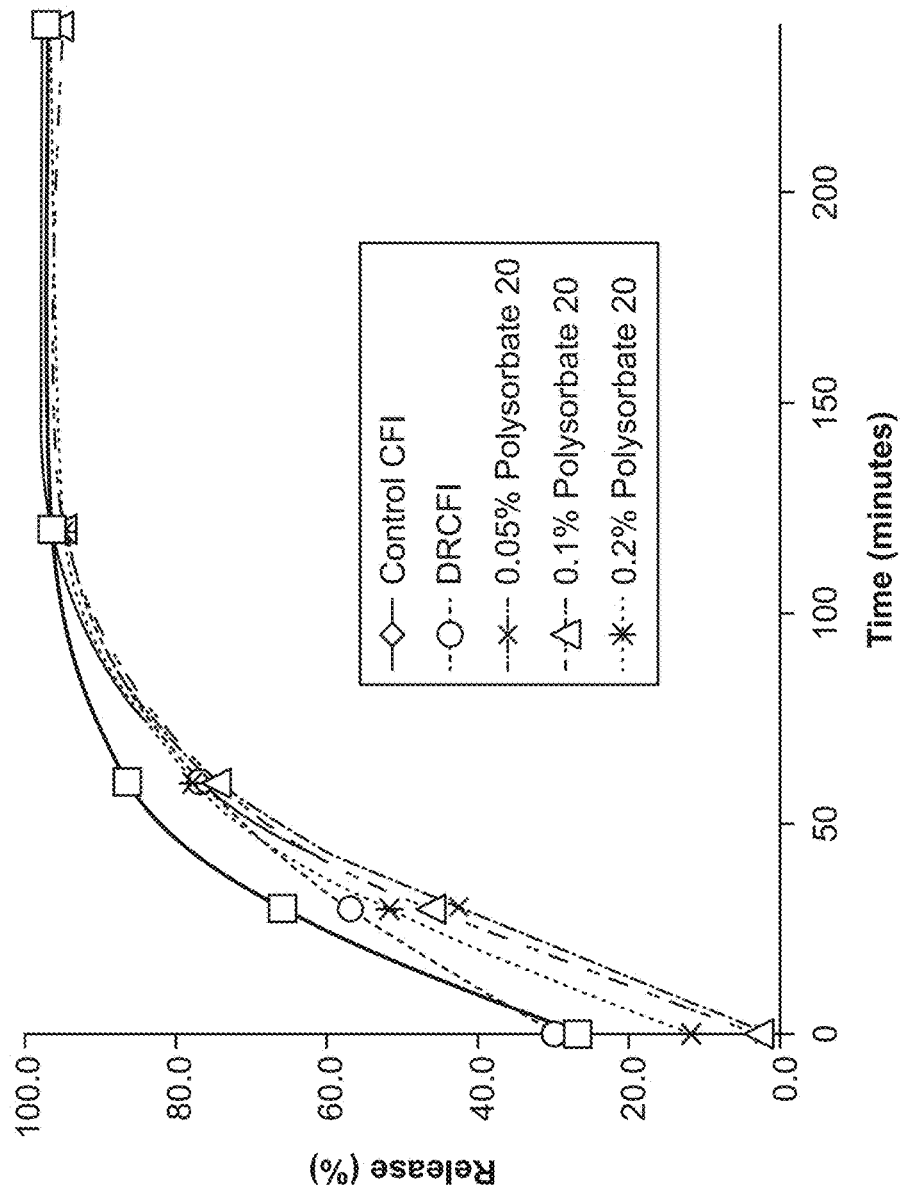
FIG. 4 includes six graphs 4A, 4B, 4C, 4D, 4E and 4F which show an evaluation of the effect of liposomal composition on the IVR assay. The release of 25 µg/mL ciprofloxacin in 50% bovine serum and 10 mM HEPES buffered saline, pH 7.4 after incubation at 37° C. for 4 h is reported. (A) IVR profiles for Control CFI (open diamonds), DRCFI (open circles), 12.5 mg/ml CFI in 0.05% polysorbate 20 (crosses), 12.5 mg/ml CFI in 0.1% polysorbate 20 (open triangles), 12.5 mg/ml CFI in 0.2% polysorbate 20 (stars), and 12.5 mg/ml CFI in 0.4% polysorbate 20 (shaded squares). (B) IVR profiles at initial time point for Control CFI (open diamonds), 12.5 mg/ml CFI in 0.4% polysorbate 20, pH 5.5 (crosses), 12.5 mg/ml CFI in 0.4% polysorbate 20, pH 5.2 (open triangles), 12.5 mg/ml CFI in 0.4% polysorbate 20, pH 4.9 (stars), and 12.5 mg/ml CFI in 0.4% polysorbate 20, pH 4.7 (shaded squares). (C) IVR profiles at 6 month time point for Control CFI (open diamonds), 12.5 mg/ml CFI in 0.4% polysorbate 20, pH 5.2 (open triangles), 12.5 mg/ml CFI in 0.4% polysorbate 20, pH 4.9 (stars), and 12.5 mg/ml CFI in 0.4% polysorbate 20, pH 4.7 (shaded squares). (D) IVR profiles at 12 month time point for Control CFI (open diamonds), 12.5 mg/ml CFI in 0.4% polysorbate 20, pH 5.2 (open triangles), 12.5 mg/ml CFI in 0.4% polysorbate 20, pH 4.9 (stars), and 12.5 mg/ml CFI in 0.4% polysorbate 20, pH 4.7 (shaded squares). (E) IVR profiles at 6 month time point after nebulization for the nebulizer residual solution and collected aerosol, respectively: 12.5 mg/ml CFI in 0.4% polysorbate 20, pH 5.2 (open diamonds and crosses), 12.5 mg/ml CFI in 0.4% polysorbate 20, pH 4.9 (open triangles and stars), and 12.5 mg/ml CFI in 0.4% polysorbate 20, pH 4.7 (shaded squares and open circles). (F) IVR profiles for Control CFI (open diamonds), DRCFI (open triangles), and 12.5 mg/ml CFI in 0.2% polysorbate 80 (open diamonds). Each value represents the mean±SD (n=2).
Figure 4B:
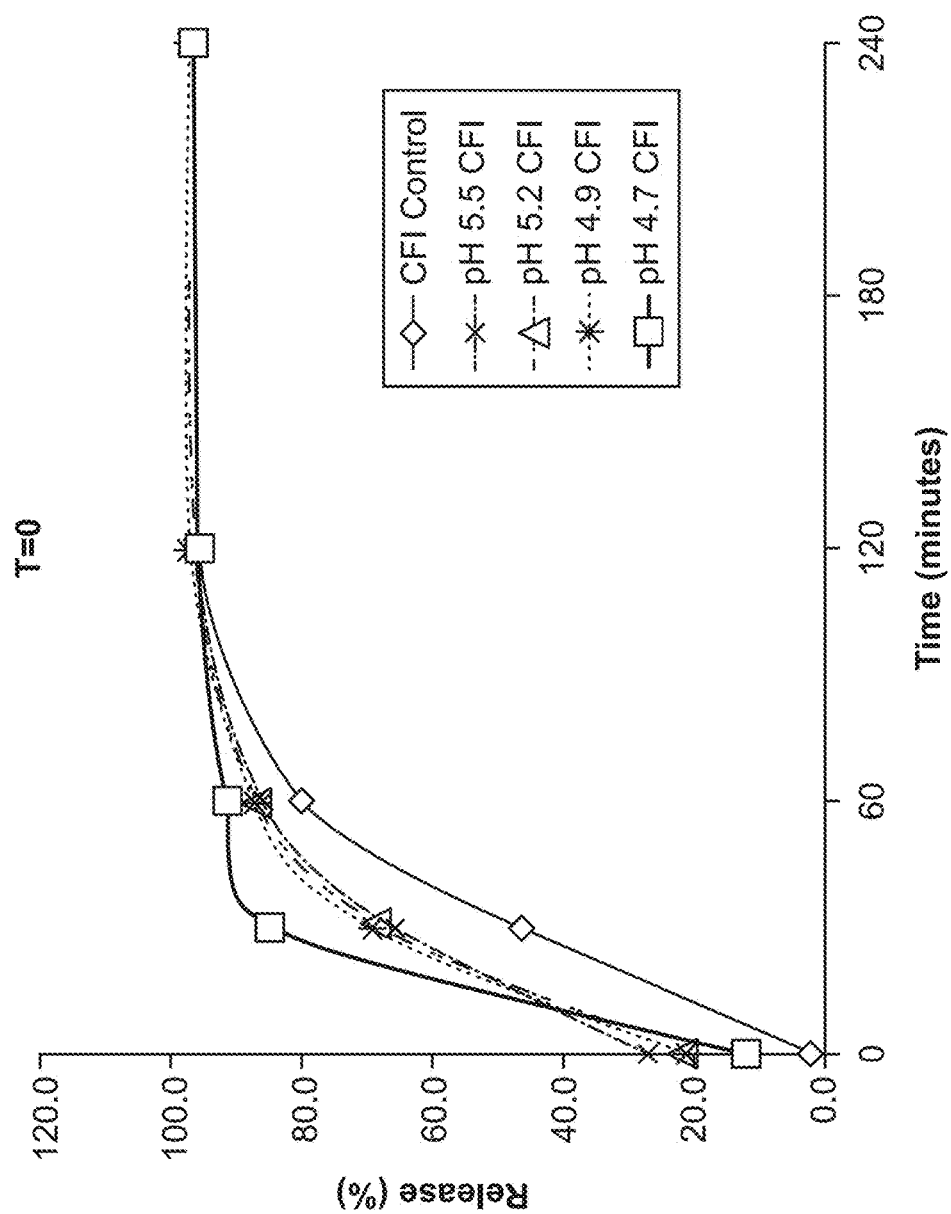

In contrast, for higher concentrations of polysorbate 20; e.g., 0.4%, there was a significant increase in the IVR release rate for 12.5 mg/ml CFI (FIG. 4A). In addition, a second population of liposomes emerged which were comparable in size, shape and lamellarity to the CFI liposomes, but had lighter shading (FIG. 3D vs. 3A). Regardless of the exact surfactant interaction and drug release mechanism for 12.5 mg/ml liposomal ciprofloxacin mixed with 0.4% polysorbate 20, it appears that the liposomes which retain encapsulated drug have an altered IVR release profile compared to CFI alone. The result we obtained for this liposome-surfactant system may be generalizable to other systems.

Another interesting result was that the amount of ciprofloxacin released from the liposomes at a constant ratio of surfactant to liposomes was not uniform (FIG. 2B). Instead, for the highest CFI concentration of 30 mg/ml, more than 95% remained encapsulated while for the lowest CFI concentration of 10 mg/ml, only 56% remained encapsulated. This is likely related to the greater hypotonicity for the 10 mg/ml CFI compared to the 30 mg/ml CFI preparations due to greater dilution with water. The resulting osmotic imbalance between the inside and the outside of the liposomes may result in osmotic swelling of the liposomes. The combination of addition of surfactant in concert with osmotic swelling appears to result in a synergistic effect with greater loss in encapsulation FIG. 2B versus 2A). After surfactant has been mixed with 30 mg/ml CFI, and allowed to equilibrate, three-fold dilution with water, keeping the ratio of surfactant to liposomes constant, did not result in much additional loss of encapsulated drug, certainly not approaching the levels for 10 mg/ml CFI (FIG. 2C). For low concentrations of polysorbate 20, up to 0.2%, there did not appear to be much effect on the IVR release rate of 12.5 mg/ml CFI suggesting that the membrane permeability and packing was not too perturbed (FIG. 4A). However, the addition of 0.4% polysorbate 20 to 12.5 mg/ml CFI led to a more rapid release of encapsulated drug in the IVR assay (FIG. 4A). The SPAN 20 and SPAN 80 surfactants were much less disruptive than the polysorbatesIn contrast, both pluronic surfactants, composed of a hydrophobic polyoxypropylene segment, flanked by two hydrophilic chains of polyoxyethylene, had very little effect on drug encapsulation (FIG. 1.

While the use of surfactants to produce therapeutic niosomes has received much attention, there are few examples in the literature where surfactant was added to phospholipid vesicles or liposomes to intentionally modify their physicochemical properties to modulate drug release. In one study, polysorbate 20, 60 or 80 was added to soy phosphatidylcholine to produce unilamellar vesicles or multilamellar aggregates (MLVs) containing caffeine as the model drug (Fadda, Baroli et al. 1998). There was no sustained release of caffeine from the unilamellar liposomes, whether or not surfactant was present, as the release profiles were identical to that for caffeine in solution (Fadda et al., 1998). In contrast, in our study using unilamellar liposomes, the presence of small amounts of polysorbate 20 or 80 had a minimal effect on the release rate while higher polysorbate concentrations caused a faster release profile in the IVR assay. The other distinguishing factor in this study is that the surfactant was added during liposome manufacture to modify their properties whereas in our study surfactant was added to the intact pre-existing liposomes.

The pH 4.7 and 4.9 preparations retained good appearance after one-year refrigerated storage in contrast to the pH 5.5 preparation which formed ciprofloxacin crystals within 48 hr. The appearance of the pH 5.2 preparation showed some small particulates but otherwise showed no further deterioration.

Figure 4C:
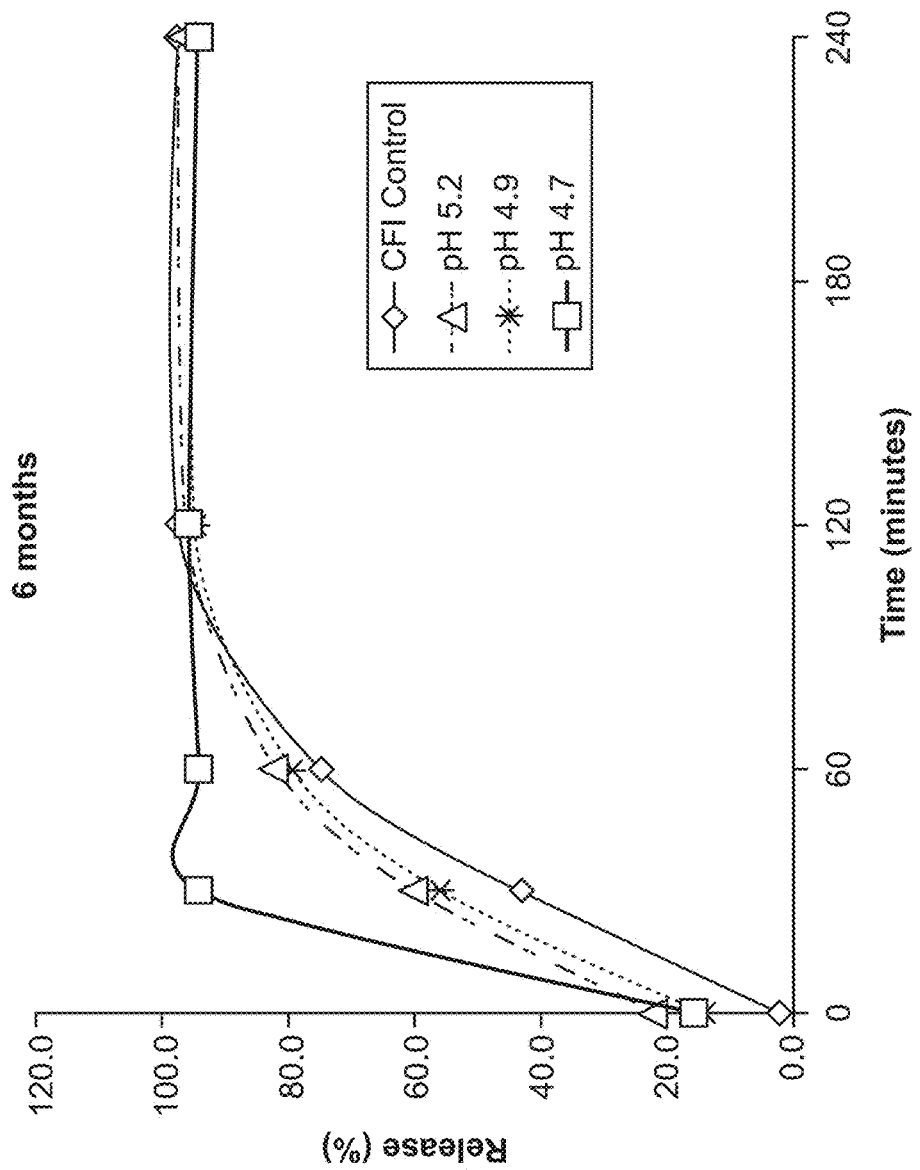
Figure 4D:
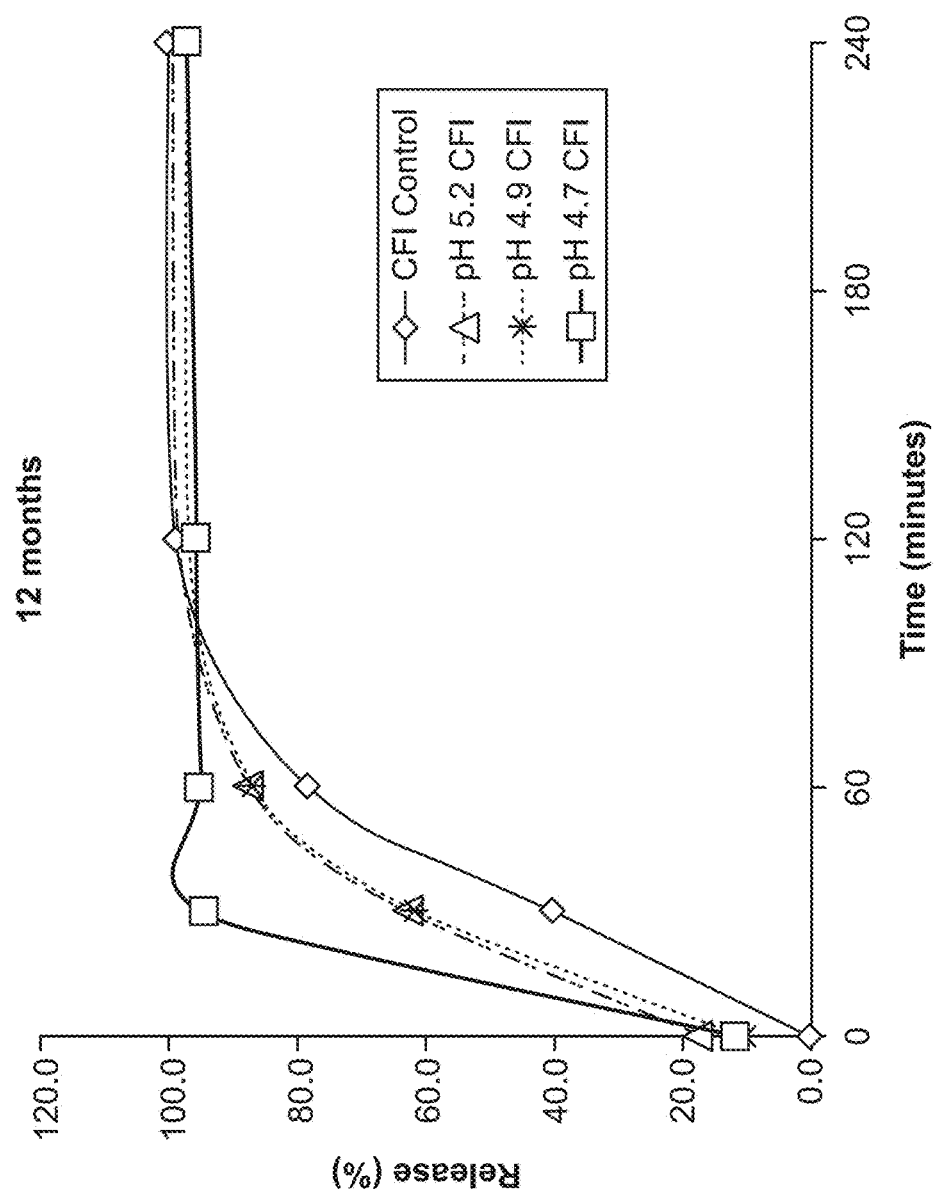
Figure 4E:
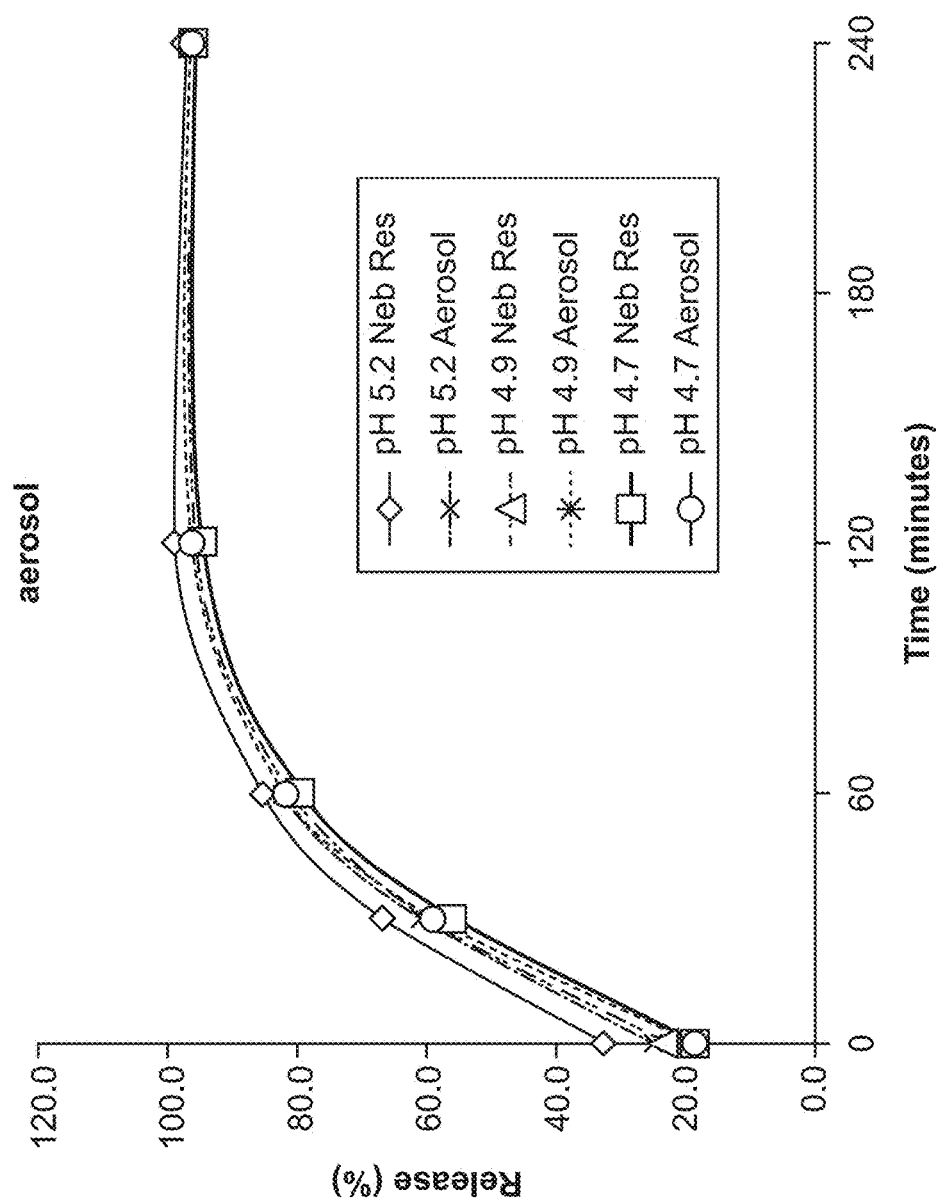

One unexpected finding was that the reduction in pH was associated with an increase in encapsulation, with greatest encapsulation for the lowest pH formulation (Table III). Once this new encapsulation state was established, it did not fluctuate during the course of the one-year refrigerated storage (Table III). There was also a slight increase in vesicle size with reduction in pH upon preparation but there were no further vesicle size changes throughout the course of the one year refrigerated storage (Table II). The IVR profiles for the liposome-surfactant preparations at pH 5.2 and 4.9 were similar to that for the pH 5.5 preparation (FIG. 4B), and retained that modified release profile through 12 months refrigerated storage (FIGS. 4C-4D). In contrast, the pH 4.7 surfactant-liposome preparation had a much faster release profile in the IVR assay (FIG. 4B) that remained unchanged after one year refrigerated storage (FIGS. 4C-4D).

Many liposomal products have been developed with the intention for inhaled administration to treat lung disease (Cipolla, et al. 2013b). However, very few were found to be robust to the nebulization process (Cipolla, et al. 2013a). Liposomes containing surfactant have historically been even less stable than traditional liposomes in response to nebulization with changes in vesicle size and/or encapsulation (Egle, et al. 2008, Elhissi, et al. 2012). Ultra-deformable liposome formulations containing salbutamol sulfate and comprised of soy PC, polysorbate 80 and cholesterol were evaluated in jet, ultrasonic and mesh nebulizers and all combinations were found to have marked losses in drug encapsulation and changes in vesicle size (Elhissi, et al. 2012). Liposomes containing cyclosporine and comprised of soy PC and polysorbate 80 were exposed to mesh nebulization and the average vesicle size doubled from 51 nm before nebulization to 107 nm after nebulization (Egle, et al. 2008). However, there was no reported loss in drug encapsulation because the poorly-soluble cyclosporine drug remained associated with the hydrophobic liposome bilayers and was not encapsulated within the liposome vesicles (Behr et al., 2009). Our liposomal ciprofloxacin formulations have already been shown to be stable to jet nebulization with no meaningful changes in vesicle size or loss in drug encapsulation (Cipolla et al., 2010, Cipolla et al., 2013a). After mesh nebulization, liposomal ciprofloxacin formulations containing 0.4% polysorbate 20 showed a small increase in mean vesicle size (by a few nm) and the drug encapsulation were normalized to 70-85% (Table VI).

Figure 4F:
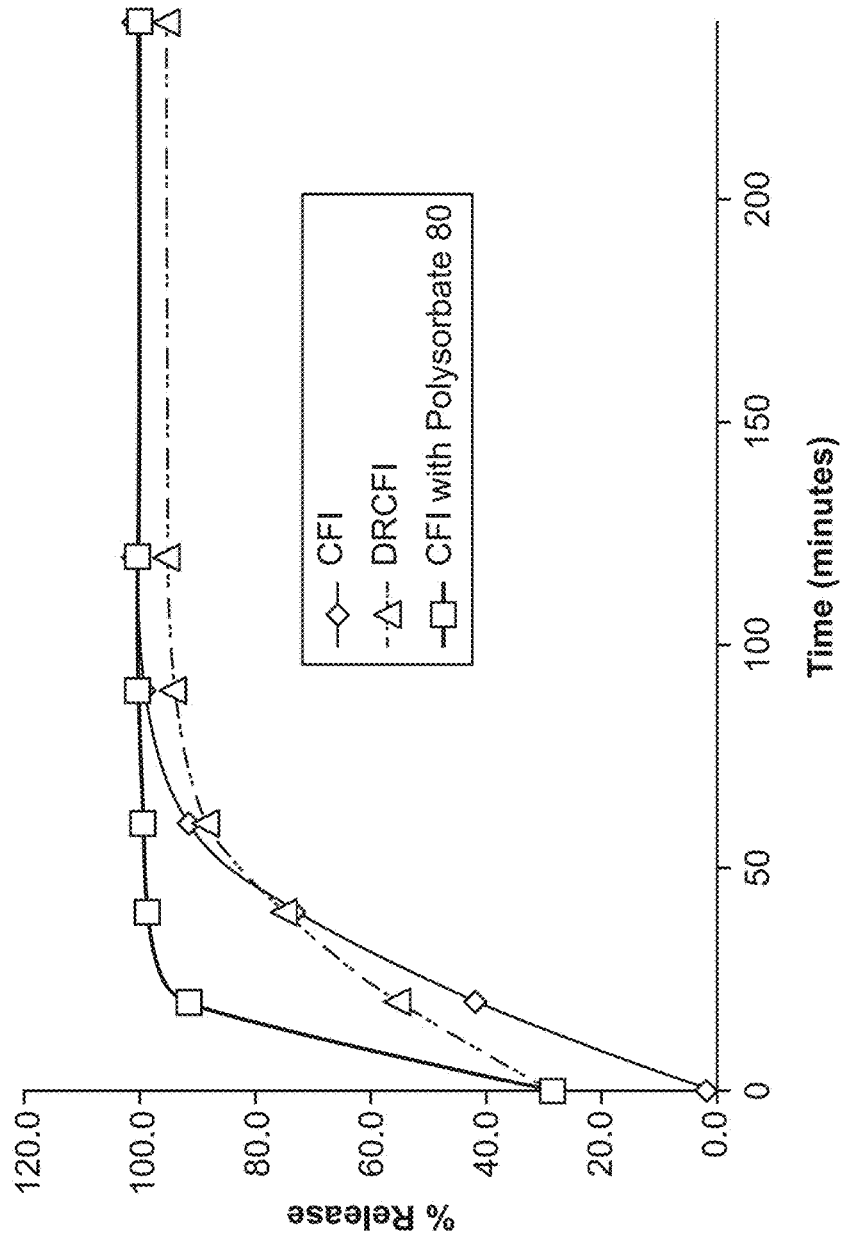

Liposomal ciprofloxacin formulations containing 0.4% polysorbate 20, or 0.2% polysorbate 80 possessed modified release properties (FIGS. 4B and 4F), and a number of formulations were found to retain those IVR characteristics after 6 months refrigerated storage and mesh nebulization (FIG. 4E).

CONCLUSION

Surfactant-liposome interactions have historically been investigated as a simplified model of solubilization and breakdown of biological membranes by surfactants. In contrast, our goal was to utilize surfactants to modify the encapsulation and release properties of liposomes. The ability to manufacture one liposomal formulation, which could be modified by addition of surfactant to support a wide range of release profiles, would provide greater flexibility than manufacturing multiple batches of liposomes, each differing in composition and with its own specific release profile. A liposomal ciprofloxacin formulation was modified by the addition of various surfactants. These formulations were characterized in terms of liposome structure by cryo-TEM imaging, vesicle size by dynamic light scattering, drug encapsulation by centrifugation-filtration, and in vitro release performance. The addition of polysorbate 20 or polysorbate 80 to liposomal ciprofloxacin, in a hypotonic environment, resulted in a concentration-dependent loss of encapsulated drug, and above 0.4% polysorbate 20, or 0.2% polysorbate 80, a modified in vitro release profile as well. This study demonstrates that the encapsulation and release properties of a liposomal formulation can be modified post manufacture by addition of judiciously-chosen surfactants in combination with osmotic swelling of the liposomes and may support a personalized approach to treating patients.

In line with the goal of personalized medicine, to tailor a product to an individual's needs so that it releases the 'right amount of drug at the right time', this strategy provides more flexibility than the alternative of manufacturing multiple batches of liposomes differing in composition to cover a broad range of desired release profiles.

While these studies on modifying the release rate of a liposomal formulation speak to the promise of tailoring therapy to an individual's needs, it is understood that other steps may be required to apply these principles in the practice of medicine. As the personalization involves relatively minor qualitative changes in the formulation and its primary purpose is to modulate the PK profile with the view to optimize the treatment efficacy and safety for each patient, this approach seems much easier to regulate than introduction of products with fundamentally different compositions or manufacturing processes. Another hurdle would be how to determine the ideal release profile for each patient. The answer clearly would depend upon the specific disease being addressed, the properties of the therapeutic being delivered, and the characteristics of the patient which demanded a personalized regimen. The total amount of drug is individualized to the patient, based on their body mass, and depending on the rate of clearance of the carrier (liposome), the rate of release of the drug from the carrier and the rate of clearance of the drug in each patient vis a vis the desired therapeutic effects and potential side-effects, the personalization for each patient could be conducted. For example, if a sputum sample from a patient indicated colonization with a bacterial strain with a higher minimum inhibitory concentration (MIC), then the most effective treatment might be a faster release profile of a liposomally encapsulated antibiotic resulting in higher ciprofloxacin concentrations in the lung to better kill the more resistant pathogen. Other characteristics of the patient or the disease status could also be measured, including the patient's height, weight, age, gender, body mass, lean body mass, Body mass index, lung function (FEV1, FVC, etc), renal clearance assessment, liver function assessment, and the nature of the disease including the pathogen that is in the sputum sample or residing in the lung, the virulence of the pathogen, and prior treatment experience and outcome. The selected formulation may also be changed if a patient reports side effects, the therapy is ineffective, new microorganisms emerge, or any combination of the above that the physician and patient believe would improve the therapeutic outcomes.

REFERENCES

Each of the following is incorporated by reference.
1. Abraham, S. A., D. N. Waterhouse, L. D. Mayer, P. R. Cullis, T. D. Madden and M. B. Bally (2005). "The liposomal formulation of doxorubicin." *Methods Enzymol* 391: 71-97.
2. Bangham A D, Standish M M, Watkins J C, Diffusion of univalent ions across the lamellae of swollen phospholipids. *J Mol Biol.* 13 (1) (1965) 238-252.
3. Boman, N. L., L. D. Mayer and P. R. Cullis (1993). "Optimization of the retention properties of vincristine in liposomal systems." *Biochim Biophys Acta* 1152(2): 253-258.
4. Bruinenberg P, Blanchard J D, Cipolla D C, Dayton F, Mudumba S, and Gonda I. (2010), Inhaled liposomal ciprofloxacin: once a day management of respiratory infections. *Respiratory Drug Delivery* 2010. pp. 73-81. Editors, Richard N. Dalby, Peter R. Byron, Joanne Peart, Julie D. Suman, Stephen J. Farr, Paul M. Young. Davis Healthcare Int'l Publishing, River Grove, Ill. Orlando, Fla., Apr. 25-29, 2010.
5. Cho, W., S. K. Wu, E. Yoon and L. Lichtenbergova (1999). "Fluorometric phospholipase assays based on polymerized liposome substrates." *Methods Mol Biol* 109: 7-17.
6. Cipolla D C, Dayton F, Fulzele S, Gabatan E, Mudumba S, Yim D, Wu H and Zwolinski R. (2010), Inhaled Liposomal Ciprofloxacin: In Vitro Properties and Aerosol Performance. *Respiratory Drug Delivery* 2010. pp. 409-414. Editors, Richard N. Dalby, Peter R. Byron, Joanne Peart, Julie D. Suman, Stephen J. Farr, Paul M. Young. Davis Healthcare Int'l Publishing, River Grove, Ill. Orlando, Fla., Apr. 25-29, 2010.
7. Cipolla D, Redelmeier T, Eastman S., Bruinenberg P, and Gonda I. (2011) Liposomes, niosomes and proniosomes—a critical update of their (commercial) development as inhaled products. *Respiratory Drug Delivery Europe* 2011, pp 41-54. Editors, Richard N. Dalby, Peter R. Byron, Joanne Peart, Julie D. Suman, Stephen J. Farr, Paul M. Young. Davis Healthcare Int'l Publishing, River Grove, Ill. Berlin, Germany, May 3-6, 2011.
8. Cipolla D, Wu H, Chan J, Chan H-K, and Gonda I. (2013a) Liposomal Ciprofloxacin for Inhalation Retains Integrity Following Nebulization. *Respiratory Drug Delivery Europe* 2013, pp 237-242. Editors, Richard N. Dalby, Peter R. Byron, Joanne Peart, Julie D. Suman, Stephen J. Farr, Paul M. Young. Davis Healthcare Int'l Publishing, River Grove, Ill. Berlin, Germany, May 21-24, 2013.
9. Cipolla D, Gonda I, and Chan H-K. (2013b) Liposomal Formulations for Inhalation. *Therapeutic Delivery*. Vol. 4, No. 8, pp. 1047-1072. doi: 10.4155/tde.13.71.
10. Cipolla D and Chan H-K. (2013) Inhaled Antibiotics to Treat Lung Infection. *Pharmaceutical Patent Analyst. Vol.* 2, No. 5, pp. 647-663.
11. Conley, J., H. Yang, T. Wilson, K. Blasetti, V. Di Ninno, G. Schnell and J. P. Wong (1997). "Aerosol delivery of liposome-encapsulated ciprofloxacin: aerosol characterization and efficacy against *Francisella tularensis* infection in mice." *Antimicrob Agents Chemother* 41(6): 1288-1292.
12. Deo, N. and P. Somasundaran (2003). "Effects of Sodium Dodecyl Sulfate on Mixed Liposome Solubilization." *Langmuir* 19(18): 7271-7275.
13. Drummond, D. C., K. Hong, J. W. Park, C. C. Benz and D. B. Kirpotin (2000). "Liposome targeting to tumors using vitamin and growth factor receptors." *Vitam Horm* 60: 285-332.
14. Egle, R., E. Bitterle, F. Gruber and M. Keller (2008). "Characterization of a liposomal ciclosporin A formulation before and after lyophilization and nebulization." AAPS National Meeting AM-08-00983.
15. Elhissi, A. M., J. Giebultowicz, A. A. Stec, P. Wroczynski, W. Ahmed, M. A. Alhnan, D. Phoenix and K. M. Taylor (2012). "Nebulization of ultradeformable liposomes: the influence of aerosolization mechanism and formulation excipients." *Int J Pharm* 436(1-2): 519-526.
16. Fadda, A. M., B. M. Baroli, A. M. Maccioni, C. Sinico, D. Valenti and F. Alhaique (1998). "Phospholipid-detergent systems: effects of polysorbates on the release of liposomal caffeine." *Il Farmaco* 53(10-11): 650-654.
17. Hamblin A J, et al., (2013) Efficacy of Inhaled Liposome-Encapsulated Ciprofloxacin Against Yersinis pestis. 19th Congress of the International Society of Aerosols in Medicine.
18. Helenius, A. and K. Simons (1975). "Solubilization of membranes by detergents." *Biochim Biophys Acta* 415(1): 29-79.
19. Johnston, M. J., S. C. Semple, S. K. Klimuk, K. Edwards, M. L. Eisenhardt, E. C. Leng, G. Karlsson, D. Yanko and P. R. Cullis (2006). "Therapeutically optimized rates of drug release can be achieved by varying the drug-to-lipid ratio in liposomal vincristine formulations." *Biochim Biophys Acta* 1758(1): 55-64.
20. Lasch, J. (1995). "Interaction of detergents with lipid vesicles." *Biochim Biophys Acta* 1241(2): 269-292.
21. Lasic, D. D., B. Ceh, M. C. Stuart, L. Guo, P. M. Frederik and Y. Barenholz (1995). "Transmembrane gradient driven phase transitions within vesicles: lessons for drug delivery." *Biochim Biophys Acta* 1239(2): 145-156.
22. Lichtenberg, D., R. J. Robson and E. A. Dennis (1983). "Solubilization of phospholipids by detergents. Structural and kinetic aspects." *Biochim Biophys Acta* 737(2): 285-304.
23. Liu, Y. and S. L. Regen (1993). "Control over vesicle rupture and leakage by membrane packing and by the aggregation state of an attacking surfactant." *Journal of the American Chemical Society* 115(2): 708-713.
24. Mayer, L. D., M. B. Bally, P. R. Cullis, S. L. Wilson and J. T. Emerman (1990). "Comparison of free and liposome encapsulated doxorubicin tumor drug uptake and antitumor efficacy in the SC115 murine mammary tumor." *Cancer Lett* 53(2-3): 183-190.
25. Memoli, A., M. C. Annesini and S. Petralito (1999). "Surfactant-induced leakage from liposomes: a comparison among different lecithin vesicles." *Int J Pharm* 184 (2): 227-235.
26. Nagawa, Y. and S. L. Regen (1992). "Surfactant-induced release from phosphatidylcholine vesicles. Regulation of rupture and leakage pathways by membrane packing." *Journal of the American Chemical Society* 114(5): 1668-1672.
27. Paternostre, M. T., M. Roux and J. L. Rigaud (1988). "Mechanisms of membrane protein insertion into liposomes during reconstitution procedures involving the use of detergents. 1. Solubilization of large unilamellar liposomes (prepared by reverse-phase evaporation) by triton X-100, octyl glucoside, and sodium cholate." *Biochemistry* 27(8): 2668-2677.
28. Polonio R E Mermel L A, Paquette G E, Sperry J F., Eradication of biofilm-forming *Staphylococcus epidermidis* (RP62A) by a combination of sodium salicylate and vancomycin. *Antimicrob Agents Chemother.* 2001 November; 45(11):3262-6.
29. Ribosa, I., M. T. Garcia, J. L. Parra, A. Maza, J. Sanchez-Leal, C. Trullas, A. Tsi, F. Balaguer and C. Pelejero (1992). "Physico-chemical modifications of liposome structures through interaction with surfactants." *Int J Cosmet Sci* 14(3): 131-149.
30. Ruiz, J., F. M. Goni and A. Alonso (1988). "Surfactant-induced release of liposomal contents. A survey of methods and results." *Biochim Biophys Acta* 937(1): 127-134.
31. Serisier D J, Bilton D, De Soyza A, Thompson P J, Kolbe J, Greville H W, Cipolla D, Bruinenberg P, and Gonda I. (2013) Inhaled, Dual-Release Liposomal Ciprofloxacin in Non-Cystic Fibrosis Bronchiectasis (ORBIT-2)—a Randomised, Double-Blind, Placebo-Controlled Trial. *Thorax.* Vol. 68, No. 9, pp. 812-817 doi: 10.1136/thoraxjnl-2013-203207
32. Thoren, P. E., O. Soderman, S. Engstrom and C. von Corswant (2007). "Interactions of novel, nonhemolytic surfactants with phospholipid vesicles." *Langmuir* 23(13): 6956-6965.
33. Velluto, D., C. Gasbarri, G. Angelini and A. Fontana (2011). "Use of simple kinetic and reaction-order measurements for the evaluation of the mechanism of surfactant-liposome interactions." *J Phys Chem B* 115(25): 8130-8137.
34. Webb, M. S., N. L. Boman, D. J. Wiseman, D. Saxon, K. Sutton, K. F. Wong, P. Logan and M. J. Hope (1998). "Antibacterial efficacy against an in vivo *Salmonella typhimurium* infection model and pharmacokinetics of a liposomal ciprofloxacin formulation." *Antimicrob Agents Chemother* 42(1): 45-52.
35. Yim D. et al., (2006). "The development of inhaled liposome-encapsulated ciprofloxacin to treat cystic fibrosis." *Respiratory Drug Delivery* 2006: 425-428.

What is claimed is:

1. A composition, comprising:
   liposomes comprised of compounds encapsulating a pharmaceutically active drug, wherein the liposomes are unilamellar, and comprised of phospholipids and cholesterol;
   a pharmaceutically active free drug;
   a pharmaceutically acceptable excipient; and
   a polysorbate surfactant which interacts with the liposomes to reduce drug encapsulation and increase drug release from the liposomes;
   wherein the weight ratio of polysorbate surfactant to liposomes is from 1:20 to 1:4;
   wherein the surfactant causes an increase in drug release rate from the liposomes of about 5% to 50% as measured by an IVR assay.

2. The composition of claim 1, wherein the composition is aerosolized into particles of formulation for inhalation into a human lung.

3. The composition of claim 1 wherein the composition is aerosolized into particles having an aerodynamic diameter in a range of 0.5 μm to 12 μm.

4. The composition of claim 3, wherein the pharmaceutically active drug is an anti-infective.

5. The composition of claim 4, wherein the anti-infective is ciprofloxacin.

6. The composition of claim 4, wherein the anti-infective is selected from the group consisting of a quinolone, a sulfonamide, an aminoglycoside, a tetracycline, para-aminobenzoic acid, a diaminopyrimidine, a beta-lactam, a beta-lactam and a beta-lactamase inhibitor, chloramphenicol, a macrolide, lincomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, and terbinafine.

7. The composition of claim 1, wherein the formulation provide a rate of release of encapsulated drug between 2 and 10% per hour, with the near complete release of drug occurring after about 1 to 24 hours and the surfactant is polysorbate 20.

8. The composition of claim 7, wherein the surfactant interacts with the liposome resulting in an increase in free drug of 1 to 50%.

9. A method of treating or ameliorating a *P. aeruginosa* infection, comprising:
   aerosolizing a composition comprised of unilamellar liposomes comprised of phospholipids and cholesterol encapsulating ciprofloxacin to create aerosolized particles having an aerodynamic diameter in a range of 0.5 microns to 12 microns; and
   allowing the particles to be inhaled;
   wherein the composition further comprises:
   free ciprofloxacin;
   a pharmaceutically acceptable excipient; and
   a polysorbate surfactant which interacts with the liposomes to reduce encapsulation of the ciprofloxacin and modulate release of the ciprofloxacin from the liposomes; and
   wherein the polysorbate surfactant interacts with the liposomes in a manner which cause the liposomes to increase their ciprofloxacin release rate by 20% to 200% as measured by an IVR assay.

10. The method of claim 9, wherein the ratio of polysorbate surfactant to liposomes by volume is between about 1:100 and 1:2.

11. The method of claim 9, wherein the polysorbate surfactant interacts with the liposomes causing a release of ciprofloxacin from the liposomes thereby increasing the amount of free ciprofloxacin by 1 to 50%.

12. A method of modulating a drug release rate of a formulation, comprising:
   providing a formulation comprised of a pharmaceutically acceptable carrier and liposomes, wherein the liposomes are comprised of a drug and phosphatidylcholine;
   adding polysorbate 20 to the formulation in an amount of 0.1 to 1% by volume thereby increasing a drug release profile of the liposomes.

13. The method of claim 12, further comprising:
   administering the formulation to a patient; and
   adjusting the amount of polysorbate 20 added based on a characteristic of the patient.

14. The method of claim 13, wherein the formulation is administered by inhalation and the patient characteristic is lung function.

15. The method of claim 13, wherein the patient characteristic is selected from the group consisting of body mass, lean body mass, height, age, gender, renal clearance assessment, liver function assessment, and determined concentration of the drug in patient blood.

16. The method of claim 13, wherein the patient characteristic is selected from the group consisting of side effects observed, type of patient infection being treated, and known minimum inhibitory concentrations for the drug.

* * * * *